US011896005B2

(12) United States Patent
Woods et al.

(10) Patent No.: US 11,896,005 B2
(45) Date of Patent: Feb. 13, 2024

(54) WARMING CRYOPRESERVED BONE

(71) Applicant: Ossium Health, Inc., San Francisco, CA (US)

(72) Inventors: Erik J. Woods, Carmel, IN (US); Brian H. Johnstone, Fishers, IN (US)

(73) Assignee: Ossium Health, Inc., San Francisco, CA (US)

( * ) Notice: Subject to any disclaimer, the term of this patent is extended or adjusted under 35 U.S.C. 154(b) by 0 days.

(21) Appl. No.: 18/155,657

(22) Filed: Jan. 17, 2023

(65) Prior Publication Data

US 2023/0232820 A1 Jul. 27, 2023

Related U.S. Application Data

(63) Continuation of application No. PCT/US2021/042064, filed on Jul. 16, 2021.

(60) Provisional application No. 63/184,109, filed on May 4, 2021, provisional application No. 63/180,625, filed on Apr. 27, 2021, provisional application No. 63/176,191, filed on Apr. 16, 2021, provisional application No. 63/113,777, filed on Nov. 13, 2020, provisional application No. 63/053,585, filed on Jul. 18, 2020.

(51) Int. Cl.
*A01N 1/02* (2006.01)
*C12N 5/0789* (2010.01)
*C12N 5/0775* (2010.01)

(52) U.S. Cl.
CPC ......... *A01N 1/0284* (2013.01); *A01N 1/0221* (2013.01); *A01N 1/0289* (2013.01); *C12N 5/0647* (2013.01); *C12N 5/0663* (2013.01); *C12N 2509/00* (2013.01)

(58) Field of Classification Search
None
See application file for complete search history.

(56) References Cited

U.S. PATENT DOCUMENTS

| | | | |
|---|---|---|---|
| 4,674,184 A | 6/1987 | Anderson | |
| 4,710,472 A | 12/1987 | Saur et al. | |
| 5,474,687 A | 12/1995 | Van Vlasselaer | |
| 5,672,346 A | 9/1997 | Srour et al. | |
| 5,766,944 A | 6/1998 | Ruiz | |
| 5,840,580 A | 11/1998 | Terstappen et al. | |
| 5,858,782 A | 1/1999 | Long et al. | |
| 6,739,112 B1 | 5/2004 | Marino | |
| 6,900,029 B1 | 5/2005 | Coulter et al. | |
| 7,470,538 B2 | 12/2008 | Laughlin et al. | |
| 7,547,210 B1 | 6/2009 | Valen | |
| 7,794,705 B2 | 9/2010 | Pecora et al. | |
| 7,883,698 B2 * | 2/2011 | Michejda | A61K 35/48 435/13 |
| 7,915,043 B2 | 3/2011 | Caligiuri et al. | |
| 7,927,785 B2 | 4/2011 | Milhem et al. | |
| 8,048,618 B2 | 11/2011 | Luk et al. | |
| 8,088,370 B2 | 1/2012 | Pecora et al. | |
| 8,343,485 B2 | 1/2013 | Pecora et al. | |
| 8,425,899 B2 | 4/2013 | Pecora et al. | |
| 8,637,005 B2 | 1/2014 | Pecora et al. | |
| 8,709,403 B2 | 4/2014 | Pecora et al. | |
| 8,956,862 B2 | 2/2015 | Pal et al. | |
| 9,034,316 B2 | 5/2015 | Pecora et al. | |
| 9,078,429 B2 | 7/2015 | McGann et al. | |
| 9,192,695 B2 | 11/2015 | Shi | |
| 9,241,959 B2 | 1/2016 | Tang | |
| 9,402,377 B2 | 8/2016 | Flavell et al. | |
| 9,409,906 B2 | 8/2016 | Sauvageau et al. | |
| 9,499,792 B2 | 11/2016 | Chretien et al. | |
| 9,504,717 B2 | 11/2016 | Strober et al. | |
| 9,533,010 B2 | 1/2017 | Pecora et al. | |
| 9,534,202 B2 | 1/2017 | Pecora et al. | |
| 9,561,253 B2 | 2/2017 | Strober et al. | |
| 9,675,643 B2 | 6/2017 | Weston et al. | |
| 9,675,644 B2 | 6/2017 | Weston et al. | |
| 9,687,511 B2 | 6/2017 | Weston et al. | |
| 9,808,558 B2 | 11/2017 | Shi | |
| 9,814,803 B2 | 11/2017 | Shi | |
| 9,828,586 B2 | 11/2017 | Tom et al. | |
| 9,945,854 B2 | 4/2018 | Altman et al. | |
| 9,963,678 B2 | 5/2018 | Tom et al. | |
| 9,974,807 B2 | 5/2018 | Strober et al. | |
| 10,047,344 B2 | 8/2018 | Poon et al. | |
| 10,076,113 B2 | 9/2018 | Chretien et al. | |
| 10,076,542 B2 | 9/2018 | Strober et al. | |
| 10,080,769 B2 | 9/2018 | Strober et al. | |
| 10,143,562 B2 | 12/2018 | Malinin | |

(Continued)

FOREIGN PATENT DOCUMENTS

| | | |
|---|---|---|
| CN | 107012119 A | 8/2017 |
| EP | 3107995 B1 | 10/2019 |

(Continued)

OTHER PUBLICATIONS

Nasca & Whelchel "Use of Cryopreserved Bone in Spinal Surgery" (1987), Spine, vol. 12, No. 3: 222-227. (Year: 1987).*
AATB. Guidance Document, in Evaluation of Body Cooling at Standard D5.400. 2013. American Association of Tissue Banks: McLean, VA. p. 13.
Ahrens et al.: Mesenchymal stem cell content of human vertebral bone marrow. Transplantation, 2004. 78(6): p. 925-929.
Aimuhem et al.: University of Cincinnati. Cryopreservation and Hyopthermal Storage of Hematopoietic Stem Cells. (2013).
Banfi et al.: Replicative aging and gene expression in long-term cultures of human bone marrow stromal cells. Tissue Eng, 2002. 8(6): p. 901-10.

(Continued)

*Primary Examiner* — Teresa E Knight
(74) *Attorney, Agent, or Firm* — Wilson Sonsini Goodrich & Rosati

(57) ABSTRACT

The present disclosure relates to, at least, a vacuum-assisted method for infiltrating cadaver bone with a cryoprotectant and a method for rapidly warming the cryopreserved cadaver bone for bone marrow processing.

22 Claims, 10 Drawing Sheets

(56) References Cited

U.S. PATENT DOCUMENTS

| | | |
|---|---|---|
| 10,159,694 B2 | 12/2018 | Strober et al. |
| 10,183,043 B2 | 1/2019 | Strober et al. |
| 10,258,648 B2 | 4/2019 | Strober et al. |
| 10,286,112 B2 | 5/2019 | Govil |
| 10,400,218 B2 | 9/2019 | Itescu et al. |
| 10,472,608 B2 | 11/2019 | Bader et al. |
| 10,513,690 B2 | 12/2019 | Ganey et al. |
| 10,550,369 B2 | 2/2020 | Tom et al. |
| 10,603,340 B2 | 3/2020 | Strober et al. |
| 10,645,921 B2 | 5/2020 | Temple et al. |
| 10,660,329 B2 | 5/2020 | Ivanovic et al. |
| 10,660,954 B2 | 5/2020 | Mitchell et al. |
| 10,669,528 B2 | 6/2020 | Rossi et al. |
| 10,995,318 B2 | 5/2021 | Woods et al. |
| 11,085,024 B2 | 8/2021 | Woods et al. |
| 11,104,882 B2 | 8/2021 | Woods et al. |
| 11,447,750 B2 | 9/2022 | Woods et al. |
| 2002/0039786 A1 | 4/2002 | Reid et al. |
| 2002/0182186 A1 | 12/2002 | Loeb |
| 2003/0082158 A1 | 5/2003 | Symonds et al. |
| 2004/0072347 A1 | 4/2004 | Schuler et al. |
| 2004/0258670 A1 | 12/2004 | Laughlin et al. |
| 2005/0233299 A1 | 10/2005 | Sawa et al. |
| 2007/0036734 A1 | 2/2007 | Tahara et al. |
| 2007/0224587 A1 | 9/2007 | Forsell et al. |
| 2010/0178279 A1 | 7/2010 | Cunningham-Rundles et al. |
| 2010/0260721 A1 | 10/2010 | McGonagie et al. |
| 2010/0310535 A1 | 12/2010 | Nakamura et al. |
| 2010/0310536 A1 | 12/2010 | Nakamura et al. |
| 2012/0052049 A1 | 3/2012 | Woods et al. |
| 2012/0276581 A1 | 11/2012 | Arav et al. |
| 2012/0276628 A1 | 11/2012 | Khan et al. |
| 2013/0011376 A1 | 1/2013 | Peled et al. |
| 2013/0216495 A1 | 8/2013 | Motlagh et al. |
| 2013/0236433 A1 | 9/2013 | Webster |
| 2013/0302293 A1 | 11/2013 | Webster |
| 2015/0216911 A1 | 8/2015 | Vines et al. |
| 2016/0000062 A1 | 1/2016 | Chen et al. |
| 2016/0089401 A1 | 3/2016 | Woods et al. |
| 2016/0101134 A1 | 4/2016 | Tang |
| 2017/0035935 A1 | 2/2017 | Uveges et al. |
| 2017/0119819 A1 | 5/2017 | Strober et al. |
| 2017/0151287 A1 | 6/2017 | Von Maltzahn et al. |
| 2017/0198257 A1 | 7/2017 | Bader et al. |
| 2017/0239390 A1 | 8/2017 | Ganey et al. |
| 2017/0240862 A1 | 8/2017 | Ganey et al. |
| 2017/0247659 A1 | 8/2017 | Ganey et al. |
| 2018/0169301 A1 | 6/2018 | Temple et al. |
| 2018/0221410 A1 | 8/2018 | Strober et al. |
| 2018/0243337 A1 | 8/2018 | Strober et al. |
| 2018/0282762 A1 | 10/2018 | Gori |
| 2018/0326122 A1 | 11/2018 | Ganey et al. |
| 2018/0334655 A1 | 11/2018 | Ganey et al. |
| 2018/0353541 A1 | 12/2018 | Delaney |
| 2019/0000877 A1 | 1/2019 | Strober et al. |
| 2019/0083530 A1 | 3/2019 | Strober et al. |
| 2019/0091262 A1 | 3/2019 | Strober et al. |
| 2019/0151506 A1 | 5/2019 | Ganey et al. |
| 2019/0191694 A1 | 6/2019 | Temple et al. |
| 2019/0192561 A1 | 6/2019 | Strober et al. |
| 2019/0192562 A1 | 6/2019 | Strober et al. |
| 2019/0298762 A1 | 10/2019 | Strober et al. |
| 2019/0336528 A1 | 11/2019 | Strober et al. |
| 2019/0343112 A1 | 11/2019 | Woods et al. |
| 2019/0345450 A1 | 11/2019 | Radtke et al. |
| 2019/0358257 A1 | 11/2019 | Strober et al. |
| 2020/0016198 A1 | 1/2020 | Jongen et al. |
| 2020/0054788 A1 | 2/2020 | Temple et al. |
| 2020/0054789 A1 | 2/2020 | Ganey et al. |
| 2020/0088718 A1 | 3/2020 | Zdanowski et al. |
| 2020/0254015 A1 | 8/2020 | Strober et al. |
| 2020/0325451 A1 | 10/2020 | Woods et al. |
| 2020/0337648 A1 | 10/2020 | Saripalli et al. |
| 2020/0399606 A1 | 12/2020 | Woods et al. |
| 2021/0214688 A1 | 7/2021 | Johnstone et al. |

FOREIGN PATENT DOCUMENTS

| | | |
|---|---|---|
| WO | WO-9307824 A1 | 4/1993 |
| WO | WO-03024215 A1 | 3/2003 |
| WO | WO-2005032251 A1 | 4/2005 |
| WO | WO-2011069117 A1 | 6/2011 |
| WO | WO-2011151452 A1 | 12/2011 |
| WO | WO-2016210292 A1 | 12/2016 |
| WO | WO-2017127755 A1 | 7/2017 |
| WO | WO-2017216775 A3 | 2/2018 |
| WO | WO-2017218948 A3 | 2/2018 |
| WO | WO-2018022651 A1 | 2/2018 |
| WO | WO-2019006328 A1 | 1/2019 |
| WO | WO-2020047236 A1 | 3/2020 |
| WO | WO-2020058324 A1 | 3/2020 |
| WO | WO-2020061180 A1 | 3/2020 |
| WO | WO-2020214400 A1 | 10/2020 |
| WO | WO-2020247341 A1 | 12/2020 |
| WO | WO-2022020210 A1 | 1/2022 |
| WO | WO-2022081896 A1 | 4/2022 |
| WO | WO-2022081909 A1 | 4/2022 |

OTHER PUBLICATIONS

Bara et al. Concise review: Bone marrow-derived mesenchymal stem cells change phenotype following in vitro culture: implications for basic research and the clinic. Stem Cells 2014 32(7) pp. 1713-1723.

Baumert et al.: Bone marrow of multiorgan donors underutilized: implications for improvement of accessibility of hematopoietic cells for transplantations. Transplantation 93(2):165-171 (2012).

Baxter et al. Study of telomere length reveals rapid aging of human marrow stromal cells following in vitro expansion. Stem Cells 22(5):675-82 (2004).

Bender et al.: Impact of freeze-thaw on isolation of viable CD34+ cells from human cadaveric bone marrow. The FASEB Journal. 34(S1) (2020) Abstract.

Bensidhoum et al.: Homing of in vitro expanded Stro-1- or Stro-1+ human mesenchymal stem cells into the NOD/SCID mouse and their role in supporting human CD34 cell engraftment. Blood, 2004. 103(9): p. 3313-9.

Berz et al.: Cryopreservation of hematopoietic stem cells. Am J Hematol 82(6):463-472 (2007).

Bieback et al.: Human Alternatives to Fetal Bovine Serum for the Expansion of Mesenchymal Stromal Cells from Bone Marrow. Stem Cells. 27(9):2331-2341 (2009).

Blashki et al.: Mesenchymal stem cells from cortical bone demonstrate increased clonal incidence, potency, and developmental capacity compared to their bone marrow-derived counterparts. J Tissue Eng, 2016. 7: p. 2041731416661196.

Blazar et al.: Successful donor cell engraftment in a recipient of bone marrow from a cadaveric donor. Blood 67(6):1655-1660 (1986).

Bork et al.: DNA methylation pattern changes upon long-term culture and aging of human mesenchymal stromal cells. Aging Cell, 2010. 9(1): p. 54-63.

Brubaker et al.: Tissue recovery practices and bioburden: a systemic review. Cell Tissue Bank. 17:561-571 (2016).

Bruder et al.: Growth kinetics, self-renewal, and the osteogenic potential of purified human mesenchymal stem cells during extensive subcultivation and following cryopreservation. J Cell Biochem, 1997. 64(2): p. 278-94.

Busilacchi et al.: A novel method to evaluate prethawing viability of cryopreserved CD34+ hematopoietic stem cells for autologous transplantation. The Journal of AABB. Transfusion. 60(7):1529-1535 (2020).

Chilima et al.: Designing the optimal manufacturing strategy for an adherent allogeneic cell therapy. BioProcess International, 2016. 14(9): p. 24-32 https://bioprocessintl.com/manufacturing/cell-therapies/designing-optimal-manufacturing-strategy-adherent-allogeneic-cell-therapy/.

Chinnadurai et al.: Immune dysfunctionality of replicative senescent mesenchymal stromal cells is corrected by IFNgamma priming. Blood Adv, 2017. 1(11): p. 628-643.

(56) References Cited

OTHER PUBLICATIONS

Choi et al.: Dissecting Cellular Heterogeneity Using Single-Cell RNA Sequencing. Mol Cells, 2019. 42(3): p. 189-199.
ClinicalTrials.gov Identifier: NCT01459107 (2011).
Cox et al.: High abundance of CD271(+) multipotential stromal cells (MSCs) in intramedullary cavities of long bones. Bone, 2012. 50(2): p. 510-7.
CRYO2018: The 55th Annual Meeting of The Society for Cryobiology. CSIC (2018) p. 1-2 Abstract.
CRYO2019: The 56th Annual Meeting of The Society for Cryobiology. CSIC (2019) p. 1-6 Abstracts.
Delloyd's Lab Tech. Standard sieves and Mesh sizes. Online publication. http://delloyd.50megs.com/moreinfo/mesh.html. pp. 2-3 (2018).
Dennis et al.: The STRO-1+ marrow cell population is multipotential. Cells Tissues Organs, 2002. 170(2-3): p. 73-82.
Digirolamo et al.: Propagation and senescence of human marrow stromal cells in culture: a simple colony forming assay identifies samples with the greatest potential to propagate and differentiate. Br J Haematol, 1999. 107(2): p. 275-81.
Dominici et al.: Minimal criteria for defining multipotent mesenchymal stromal cells. The International Society for Cellular Therapy position statement. Cytotherapy, 2006. 8(4): p. 315-7.
Donnenberg et al.: Clinical implementation of a procedure to prepare bone marrow cells from cadaveric vertebral bodies. Regen Med, 2011. 6(6): p. 701-6.
Donnenberg: Working with Bone Marrow on a Grand Scale. McGowan Retreat. Mar. 2011.
Du et al.: Rational Design of a Fluorescent Hydrogen Peroxide Probe Based on the Umbelliferone Fluorophore. Tetrahedron Letters. 49(19):3045-3048 (2008) DOI:10.1016/j.tetlet.2008.03.063.
Dykstra et al.: Concise Review: Fat and Furious: Harnessing the Full Potential of Adipose-Derived Stromal Vascular Fraction. Stem Cells Trans! Med, 2017. 6(4): p. 1096-1108.
Eagle et al.: Assessment of an improved bone washing protocol for deceased donor human bone. Cell Tissue Bank. 16:83-90 (2014) DOI:10.1007/s10561-014-9443-z.
Eckardt et al.: Comparison of engraftment and acute GVHD in patients undergoing cryopreserved or fresh allogeneic BMT. Bone Marrow Transplant, 1993. 11(2): p. 125-31.
Ferrari et al.: Beta regression for modeling rates and proportions. J. Applied Statistics, 2004. 31(7): p. 799-815.
Ferrebee et al.: The Collection, Storage and Preparation of Viable Cadaver Marrow for Intravenous Use. Blood. 14(2):140-147 (1959).
Flood et al.: Does practice make perfect? Part 1: The relations between hospital volume and outcomes for selected diagnostic categories. Medical Care, 1984. 22(2): p. 98-114.
Flood et al.: Does practice make perfect? Part II: The relation between volumes and other hospital characteristics. Medical Care, 1984. 22(2): p. 115-125.
Fragkakis et al., Vertebral body versus iliac crest bone marrow as a source of multipotential stromal cells: comparison of processing techniques, tri-lineage differentiation and application on a scaffold for spine fusion. PLoS One 13(5): e0197969 [1-20] (2018).
Fresenius Kabi Ag. 510(k) Summary. Bone Marrow Collection Stand. (2017) https://www.fda.gov/media/106490/download.
Fu et al.: Lymphohematopoietic graft-versus-host responses promote mixed chimerism in patients receiving intestinal transplantation. J Clin Invest . 131(8):e141698 (2021) doi: 10.1172/JCI141698.
Galipeau et al.: International Society for Cellular Therapy perspective on immune functional assays for mesenchymal stromal cells as potency release criterion for advanced phase clinical trials. Cytotherapy, 2016. 18(2): p. 151-9.
Galipeau et al.: Mesenchymal Stromal Cells: Clinical Challenges and Therapeutic Opportunities. Cell Stem Cell, 2018. 22(6): p. 824-833.
GE Healthcare Life Sciences. Cell Separation Media Reference (2014).

Gorantla et al.: Development and validation of a procedure to isolate viable bone marrow cells from the vertebrae of cadaveric organ donors for composite organ grafting. Cytotherapy, 2012. 14(1): p. 104-13.
Gronthos et al.: Molecular and cellular characterisation of highly purified stromal stem cells derived from human bone marrow. J Cell Sci, 2003. 116(Pt 9): p. 1827-35.
Guan et al., Comparison of biological characteristics of mesenchymal stem cells derived from the human umbilical cord and decidua parietalis. Mol Med Rep. 20(1):633-639 (2019).
Han et al.: Optimization of human umbilical cord mesenchymal stem cell isolation and culture methods. Cytotechnology. 65(5):819-827 (2013).
Harrel Jr.: Regression modeling strategies with applications to linear models, logistic regression, and survival analysis. 2nd ed. Springer Series in Statistics. 2001, New York: Springer. 582.
Harrison et al.: Cell therapy-processing economics: small-scale microfactories as a stepping stone toward large-scale macrofactories. Regen Med, 2018. 13(2): p. 159-173.
Heathman et al.: Characterization of human mesenchymal stem cells from multiple donors and the implications for large scale bioprocess development. Biochemical Engineering Journal, 2016. 108: p. 14-23.
Hemacare Corporation. Isolation of Peripheral Blood Mononuclear Cells (PBMCs) Using a Density Gradient Reagent. Technical Protocol. PROT-IPBMC-V1.1 1018 (2016).
Hibino et al.: Comparison of Human Bone Marrow Mononuclear Cells Isolation Methods for Creating Tissue-Engineered Vascular Grafts: Novel Filter System Versus Traditional Density Centrifugation Method. Tissue Engineering. Part C:17(10) (2011).
Hotta et al.: Long-term Nonhuman Primate Renal Allograft Survival Without Ongoing Immunosuppression in Recipients of Delayed Donor Bone Marrow Transplantation. Transplantation, 2018. 102(4): p. e128-e136.
Hunt. Cryopreservation of Human Stem Cells for Clinical Application: A Review. Transfus Med Hemother 38(2):107-123 (2011).
Hwang et al.: Single-cell RNA sequencing technologies and bioinformatics pipelines. Exp Mol Med, 2018. 50(8): p. 96.
Johnstone: Edit Identification and Characterization of a Large Source of Primary Mesenchymal Stem Cells Tightly Adhered to Bone Surfaces of Human Vertebral Body Marrow Cavities. ISSCR Abstract (2020).
Johnstone et al., A large-scale bank of organ donor bone marrow and matched mesenchymal stem cells for promoting immunomodulation and transplant tolerance. Front Immunol. 12:622604 [1-11] (2021).
Johnstone et al., Functional interaction between p53 and the interferon-inducible nucleoprotein IFI 16. Oncogene 19(52):6033-6042 (2000).
Johnstone et al.: Identification and characterization of a large source of primary mesenchymal stem cells tightly adhered to bone surfaces of human vertebral body marrow cavities. Cytotherapy. (2020) 1-12.
Johnstone et al.: Identification and characterization of a large source of primary mesenchymal stem cells tightly adhered to bone surfaces of human vertebral body marrow cavities. Cytotherapy. 22:617-628 (2020).
Jones et al Large-scale extraction and characterization of CD271+ multipotential stromal cells from trabecular bone in health and osteoarthritis: implications for bone regeneration strategies based on uncultured or minimally cultured multipotential stromal cells. Arthritis Rheum 2010 62(7) pp. 1944-1954.
Jossen et al.: Manufacturing human mesenchymal stem cells at clinical scale: process and regulatory challenges. Appl Microbiol Biotechnol, 2018. 102(9): p. 3981-3994.
Kawai et al.: Long-term results in recipients of combined HLA-mismatched kidney and bone marrow transplantation without maintenance immunosuppression. Am J Transplant, 2014 14(7) pp. 1599-1611.
Kenyon et al.: Effect of depletion of class II bright cells on the immunogenicity and stem cell content of human vertebral body bone marrow. Transplant Proc 27(6):3419 (1995).
Knebel et al.: Allocation of scarce resources after a nuclear detonation: setting the context. Disaster Med Public Health Prep, 2011. 5 Suppl 1: p. S20-31.

(56) References Cited

OTHER PUBLICATIONS

Lechanteur et al.: Large-scale clinical expansion of mesenchymal stem cells in the GMP-compliant, closed automated Quantum(R) cell expansion system: Comparison with expansion in traditional T-flasks. Stem Cell Research & Therapy, 2014. 4(8): p. 1-11.
Li et al.: Therapeutic Delivery Specifications Identified Through Compartmental Analysis of a Mesenchymal Stromal Cell-Immune Reaction. Sci Rep, 2018. 8(1): p. 6816.
Linch et al.: Bone marrow processing and cryopreservation. J. Clin Pathology. 35(2):186-190 (1982).
Lioznov et al.: Transportation and cryopreservation may impair haematopoietic stem cell function and engraftment of allogeneic PBSCs, but not BM. Bone Marrow Transplant, 2008. 42(2): p. 121-8.
Lipsitz et al.: A roadmap for cost-of-goods planning to guide economic production of cell therapy products. Cytotherapy, 2017. 19(12): p. 1383-1391.
Lockhart et al.: Use of Freshly Isolated Human Adipose Stromal Cells for Clinical Applications. Aesthet Surg J, 2017. 37(suppl_3): p. S4-S8.
Long et al Accumulation of CD11b+ Gr-1+ cells in the lung, blood and bone marrow of mice infected with highly pathogenic H5N1 and H1N1 influenza viruses. Archives of Virology 158(6) 1305-22 (2013).
McCarthy et al.: Tissue dissociation enzymes for isolating human islets for transplantation: factors to consider in setting enzyme acceptance criteria. Transplantation. 91(2):137-145 (2011).
Mendicino et al.: MSC-based product characterization for clinical trials: an FDA perspective. Cell Stem Cell, 2014. 14(2): p. 141-5.
Michalova et al.: Hematopoietic Stem Cells Survive Circulation Arrest and Reconstitute Hematopoiesis in Myeloablated Mice. Biol of Blood and BM Transplantation. 17(9):1273-1281 (2011).
Miller et al.: Phenotypic and Functional Equivalency of Digested Bone Marrow Mesenchymal Stem Cells to Aspirated Bone Marrow Mesenchymal Stem Cells. FASEB. 33(S1) (2019) Abstract.
Miltenyi Biotec: Isolation of Mononuclear Cells from human bone marrow aspirates by density gradient centrifugation. (2008).
Mizukami et al.: Technologies for large-scale umbilical cord-derived MSC expansion: Experimental performance and cost of g000ds analysis. Biochemical Engineering Journal, 2018. 135: p. 36-48.
Moravcikova et al.: Proteomic Profiling of Native Unpassaged and Culture-Expanded Mesenchymal Stromal Cells (MSC). Cytometry A, 2018. 93(9): p. 894-904.
Morgenstern et al.: Post-thaw viability of cryopreserved peripheral blood stem cells (PBSC) does not guarantee functional activity: important implications for quality assurance of stem cell transplant programmes. Br J Haematol 174(6):942-951 (2016).
Muraglia et al.: Clonal mesenchymal progenitors from human bone marrow differentiate in vitro according to a hierarchical model. J Cell Sci, 2000. 113 (Pt 7): p. 1161-6.
Oetjen et al.: Human bone marrow assessment by single-cell RNA sequencing, mass cytometry, and flow cytometry. JCI Insight. 3(23):7 e124928 (2018).
Olsen et al.: Peak MSC-Are We There Yet? Front Med (Lausanne), 2018. 5: p. 178.
Oseni et al.: Optimization of chondrocyte isolation and characterization for large-scale cartilage tissue engineering. Journal of Surgical Research. 181:41-48 (2013).
PCT/US2020/025778 International Preliminary Report on Patentability dated Oct. 28, 2021.
PCT/US2020/025778 International Search Report and Written Opinion dated Sep. 16, 2020.
PCT/US2021/042064 International Preliminary Report on Patentability dated Feb. 2, 2023.
PCT/US2021/042064 International Search Report and Written Opinion dated Oct. 26, 2021.
PCT/US2021/055066 International Search Report and Written Opinion dated Dec. 23, 2021.
PCT/US2021/055081 International Search Report and Written Opinion dated Jan. 20, 2021.
PCT/US2021/064152 International Search Report and Written Opinion dated Mar. 30, 2022.
Pennington et al.: Evaluation of a Sterling Cycle Controlled Rate Freezing Device for Simultaneous Cryopreservation of Multiple Units. Cryobiology. 91:146-197 (2019) Abstract.
Pereira et al.: Impact of allogeneic stem cell manufacturing decisions on cost of goods, process robustness and reimbursement. Biochemical Engineering Journal, 2018. 137: p. 132-151.
Picard et al.: Cook, Cross-validation of regression models. J. Am. Stat. Assoc, 1984. 79(428):9 pg.
Pittenger et al.: Multilineage potential of adult human mesenchymal stem cells. Science, 1999. 284(5411): p. 143-7.
Quah et al.: Monitoring lymphocyte proliferation in vitro and in vivo with the intracellular fluorescent dye carboxyfluorescein diacetate succinimidyl ester. Nat Protoc, 2007. 2(9): p. 2049-56.
Redaelli et al.: From cytogenomic to epigenomic profiles: monitoring the biologic behavior of in vitro cultured human bone marrow mesenchymal stem cells. Stem Cell Res Ther, 2012. 3(6): p. 47.
Rybka et al.: Hematopoietic progenitor cell content of vertebral body marrow used for combined solid organ and bone marrow transplantation. Transplantation, 1995. 59(6): p. 871-4.
Saegeman et al.: Influence of postmordem time on the outcome of blood cultures among cadavric tissue donors. Eur J Microbiol Infect Dis. 28:161-168 (2009).
Schneeberger et al.: Upper-extremity transplantation using a cell-based protocol to minimize immunosuppression. Ann Surg, 2013. 257(2): p. 345-51.
Schwartz et al.: Explanatory and pragmatic attitudes in therapeutical trials. J Chronic Dis, 1967. 20(8): p. 637-48.
Sherry et al.: The Influence of Warm Ischemic Time on the Viability of Deceased Organ Donor Derived Bone Marrow. The FASEB Journal. 32(S1) Abstract (2018).
Shu et al.: Development of a reliable low-cost controlled cooling rate instrument for the cryopreservation of hematopoietic stem cells. Cytotherapy 12(2):161-169 (2010).
Siclari et al.: Mesenchymal progenitors residing close to the bone surface are functionally distinct from those in the central bone marrow. Bone, 2013. 53(2): p. 575-86.
Simaria et al.: Allogeneic cell therapy bioprocess economics and optimization: single-use cell expansion technologies. Biotechnol Bioeng, 2014. 111(1): p. 69-83.
Simmons et al.: Identification of stromal cell precursors in human bone marrow by a novel monoclonal antibody, STRO-1. Blood, 1991. 78(1): p. 55-62.
Soderdahl et al.: Cadaveric bone marrow and spleen cells for transplantation. Bone Marrow Transplant, 1998. 21(1): p. 79-84.
Spitzer et al.: Twenty Year Follow Up of Histocompatibility Leukocyte Antigen-Matched Kidney and Bone Marrow Co-Transplantation for Multiple Myeloma with End Stage Renal Disease: Lessons Learned. Transplantation, 103(11): 2366-2372 (2019).
Squillaro et al.: Clinical Trials with Mesenchymal Stem Cells: An Update. Cell Transplant, 2016. 25(5): p. 829-48.
Stenn et al.: Dispase, a Neutral Protease from Bacillus Polymyxa, Is a Powerful Fibronectinase and Type IV Collagenase. J Invest Dermatol. 93(2):287-290 (1989).
Stockschlader et al.: Long-term follow-up of leukaemia patients after related cryopreserved allogeneic bone marrow transplantation. British Journal of Haematology. 96:382-386 (1997).
Stockschlader et al.: Use of cryopreserved bone marrow in allogeneic bone marrow transplantation. Bone Marrow Transplant, 1995. 15(4): p. 569-72.
Stockschlader et al.: Use of cryopreserved bone marrow in unrelated allogeneic transplantation. Bone Marrow Transplant, 1996. 17(2): p. 197-9 (Abstract).
Suire et al.: Isolation of the stromal-vascular fraction of mouse bone marrow markedly enhances the yield of clonogenic stromal progenitors. Blood. 119(11):e86-e95 (2012).
Sutherland et al.: The ISHAGE guidelines for CD34+ cell determination by flow cytometry. International Society of Hematotherapy and Graft Engineering. J Hemather, 1996. 5(3): p. 213-26.

(56) References Cited

OTHER PUBLICATIONS

Thomas et al.: Intravenous infusion of bone marrow in patients receiving radiation and chemotherapy. N Engl J Med 257(11):491-496 (1957).
Thompson et al.: Time and Temperature Dependent Ficoll Separation of Aged Whole Blood Neutrophils. The FASEB Journal. 33(S1) Abstract (2019).
Thompson: Preparing Skeletons for Research and Teaching from Preserved Human Specimens. Thesis. pp. 1-162 (2015).
Urso et al.: Short-term Preservation of Mouse Bone Marrow at Refrigeration and Room Temperature for Irradiation Experiments. J App Physiol. 10(2):314-316 (1957).
U.S. Appl. No. 16/734,713 Office Action dated Jun. 9, 2022.
U.S. Appl. No. 17/013,379 Office Action dated Feb. 18, 2021.
U.S. Appl. No. 17/013,379 Restriction Requirement dated Dec. 14, 2020.
U.S. Appl. No. 17/013,389 Final Office Action dated Feb. 19, 2021.
U.S. Appl. No. 17/013,389 First Action Interview dated Dec. 11, 2020.
U.S. Appl. No. 17/013,389 Non-Final Office Action dated Apr. 7, 2021.
U.S. Appl. No. 17/013,395 Final Office Action dated Mar. 12, 2021.
U.S. Appl. No. 17/013,395 Final Office Action dated Sep. 27, 2021.
U.S. Appl. No. 17/013,395 First Action Interview dated Dec. 1, 2020.
U.S. Appl. No. 17/013,395 Non-Final Office Action dated Apr. 13, 2021.
U.S. Appl. No. 17/013,395 Non-Final Office Action dated Jun. 17, 2022.
U.S. Appl. No. 17/013,400 Final Office Action dated Sep. 2, 2021.
U.S. Appl. No. 17/013,400 First Action Interview dated Dec. 28, 2020.
U.S. Appl. No. 17/013,400 Non-Final Office Action dated Apr. 13, 2021.
U.S. Appl. No. 17/013,407 Office Action dated Dec. 18, 2020.
U.S. Appl. No. 17/013,407 Restriction Requirement dated Nov. 10, 2020.
U.S. Appl. No. 17/684,259 Office Action dated Jun. 13, 2022.
U.S. Appl. No. 17/684,277 Office Action dated Jun. 23, 2022.
Walter et al.: Molecular and Functional Phenotypes of Human Bone Marrow-Derived Mesenchymal Stromal Cells Depend on Harvesting Techniques. Int J. of Molecular Sciences. 23.4382:1-12 (2020).
Warwick et al.: Collagenase Clostridium histolyticum: emerging practice patterns and treatment advances. Journal of Plastic Surgery and Hand Surgery. 50(5):251-326 (2016).
Weinstock et al.: Radiologic and nuclear events: contingency planning for hematologists/oncologists. Blood, 2008. 111(12): p. 5440-5.
Woods et al.: Ischemia considerations for the development of an organ and tissue donor derived bone marrow bank. Journal of Translational Medicine. 18:300 (2020) 11 pages.
Woods et al.: Off the shelf cellular therapeutics: Factors to consider during cryopreservation and storage of human cells for clinical use. Cytotherapy, 2016. 18(6): p. 697-711.
Woods et al.: Packaging considerations for biopreservation. Transfusion Medicine and Hemotherapy 38(2):149-156 (2011).
Woods et al The learning curve and the cost of heart transplantation Health Ser Res 1992 27(2) p. 219-38.
Wright, T., Factors affecting the cost of airplanes. J Aeronautical Sciences, 1936. 3(2): pp. 122-128.
Wuchter et al.: Standardization of Good Manufacturing Practice-compliant production of bone marrow-derived human mesenchymal stromal cells for immunotherapeutic applications. Cytotherapy, 2014. 17(2): p. 128-39.
Yamada et al.: Overcoming memory T-cell responses for induction of delayed tolerance in nonhuman primates. Am J Transplant, 2012. 12(2): p. 330-40.
Yusop et al.: Isolation and Characterisation of Mesenchymal Stem Cells from Rat Bone Marrow and the Endosteal Niche: A Comparative Study. Stem Cells Int, 2018. 2018: p. 6869128.

\* cited by examiner

WARMING CRYOPRESERVED BONE

CROSS-REFERENCE TO RELATED APPLICATIONS

This application is a continuation of International Application No. PCT/US2021/042064, filed Jul. 16, 2021, which claims the benefit of U.S. Provisional Application No. 63/053,585, filed Jul. 18, 2020; U.S. Provisional Application No. 63/113,777, filed Nov. 13, 2020; U.S. Provisional Application No. 63/176,191, filed Apr. 16, 2021; U.S. Provisional Application No. 63/180,625, filed Apr. 27, 2021; and U.S. Provisional Application No. 63/184,109, filed May 4, 2021. The entire contents of each of the five priority applications are expressly incorporated herein by reference.

STATEMENT AS TO FEDERALLY SPONSORED RESEARCH

This invention was made with government support under HL142418 awarded by the National Institutes of Health. The government has certain rights in the invention.

BACKGROUND

Bone marrow is a rich and diverse source of stem and progenitor cells for multiple therapeutic and medical research uses. Obtaining bone marrow traditionally has been restricted to aspirating small volumes (~100 ml) from living donors. A vastly more abundant source of bone marrow can be obtained from cadaver donors. However, multiple barriers have prevented mainstream use of cadaveric bone marrow for transplantation. Significant barriers relate, at least, to the freezing cadaver bone and later recovery of viable cells from the cadaver bone. In particular, there are challenges with respect to obtaining high numbers of good quality, viable cells, such as hematopoietic stem cells (HSCs), from frozen donor bone. The present disclosure overcomes these significant barriers.

SUMMARY

The present disclosure provides new methods for cryopreserving cadaver bone and for later thawing of cryopreserved cadaver bone. These methods, individually or when combined, provide efficient and on-demand extraction of bone marrow cells from cadaveric bone. Moreover, these methods allow for the generation of a large "smart bank" in which cadaver bone is initially typed and cryopreserved with minimal manipulation and cost; these are followed by long-term cold storage until a recipient is found, whereupon the cadaver bone is thawed and processed under GMP conditions. This smart bank will complement the bone marrow registry and cord blood banks, helping save the lives of thousands of patients who die each year where an early bone marrow transplant could have helped, and ameliorate severe health disparities in hematopoietic stem cell transplantation (HSCT), especially for minorities and women who have had children.

An aspect of the present disclosure is a method for cryopreserving a cadaver bone. The method comprises steps of: (a) placing a cadaver bone in a closed container comprising a cryoprotectant solution; (b) reducing the pressure in the closed container, and optionally, holding the closed container at reduced pressure, to remove at least a portion of the water present in the cadaver bone; (c) raising the pressure in the closed container and holding the closed container at a raised pressure to allow infiltration of the cryoprotectant solution into the cadaver bone; (d) removing the cadaver bone from the closed container; and (e) chilling the cadaver bone to a temperature at least below 0° C., thereby cryopreserving the cadaver bone.

Another aspect of the present disclosure is a method for rapidly warming cadaver bone for providing bone marrow or a derivative thereof. The method comprising steps of: obtaining a cryopreserved cadaver bone; dividing the cryopreserved cadaver bone to obtain fragments of the cryopreserved bone; transferring the fragments of the cryopreserved bone into a grinding medium having a temperature of from about 35° C. to about 45° C. for a time sufficient to warm the cadaver bone fragments to a surface temperature of about 20° C.

Yet another aspect of the present disclosure is a method comprising steps of: (a) placing a cadaver bone in a closed container comprising a cryoprotectant solution; (b) reducing the pressure in the closed container, and optionally, holding the closed container at reduced pressure, to remove at least a portion of the water present in the cadaver bone; (c) raising the pressure in the closed container and holding the closed container at a raised pressure to allow infiltration of the cryoprotectant solution into the cadaver bone; (d) removing the cadaver bone from the closed container; (e) chilling the cadaver bone to a temperature at least below 0° C., thereby cryopreserving the cadaver bone; (f) storing the cryopreserved cadaver bone at a temperature at least below 0° C.; (g) dividing the cryopreserved cadaver bone to obtain fragments of the cryopreserved bone; and (h) transferring the fragments of the cryopreserved bone into a grinding medium having a temperature of from about 35° C. to about 45° C. for a time sufficient to warm the cadaver bone fragments to a surface temperature of about 20° C.

In an aspect, the present disclosure provides a method comprising steps of: (a) placing a cadaver bone in a closed container comprising a cryoprotectant solution; (b) reducing the pressure in the closed container, and optionally, holding the closed container at reduced pressure, to remove at least a portion of the water present in the cadaver bone; (c) raising the pressure in the closed container and holding the closed container at a raised pressure to allow infiltration of the cryoprotectant solution into the cadaver bone; (d) removing the cadaver bone from the closed container; (e) chilling the cadaver bone to a temperature at least below 0° C., thereby cryopreserving the cadaver bone; (f) storing the cryopreserved cadaver bone at a temperature at least below 0° C.; (g) dividing the cryopreserved cadaver bone to obtain fragments of the cryopreserved bone; (h) transferring the fragments of the cryopreserved bone into a grinding medium having a temperature of from about 35° C. to about 45° C. for a time sufficient to warm the cadaver bone fragments to a surface temperature of about 20° C.; (i) grinding warmed cadaver bone fragments to obtain ground cadaver bone; (j) filtering the ground cadaver bone, thereby producing a filtered product comprising bone marrow cells; and (k) collecting the bone marrow cells, thereby obtaining extracted bone marrow cells.

In another aspect, the present disclosure provides a method comprising steps of: (a) placing a cadaver bone in a closed container comprising a cryoprotectant solution; (b) reducing the pressure in the closed container, and optionally, holding the closed container at reduced pressure, to remove at least a portion of the water present in the cadaver bone; (c) raising the pressure in the closed container and holding the closed container at a raised pressure to allow infiltration of the cryoprotectant solution into the cadaver bone; (d)

removing the cadaver bone from the closed container; (e) chilling the cadaver bone to a temperature at least below 0° C., thereby cryopreserving the cadaver bone; (f) storing the cryopreserved cadaver bone at a temperature at least below 0° C.; (g) dividing the cryopreserved cadaver bone to obtain fragments of the cryopreserved bone; (h) transferring the fragments of the cryopreserved bone into a grinding medium having a temperature of from about 35° C. to about 45° C. for a time sufficient to warm the cadaver bone fragments to a surface temperature of about 20° C.; (i) grinding warmed cadaver bone fragments to obtain ground cadaver bone; (j) filtering the ground cadaver bone, thereby producing a filtered product comprising bone marrow cells and a captured ground bone; (k) collecting the bone marrow cells, thereby obtaining extracted bone marrow cells; and (l) extracting vertebral bone adherent mesenchymal stromal/stem cells (vBA-MSC) from the captured ground bone by contacting the captured ground bone with a digestion solution.

In yet another aspect, the present disclosure provides a method comprising steps of: (a) placing a cadaver bone in a closed container comprising a cryoprotectant solution; (b) reducing the pressure in the closed container, and optionally, holding the closed container at reduced pressure, to remove at least a portion of the water present in the cadaver bone; (c) raising the pressure in the closed container and holding the closed container at a raised pressure to allow infiltration of the cryoprotectant solution into the cadaver bone; (d) removing the cadaver bone from the closed container; (e) chilling the cadaver bone to a temperature at least below 0° C., thereby cryopreserving the cadaver bone; (f) storing the cryopreserved cadaver bone at a temperature at least below 0° C.; (g) transferring the cryopreserved cadaver bone into a grinding medium having a temperature of from about 35° C. to about 45° C. for a time sufficient to warm the cadaver bone fragments to a surface temperature of about 20° C.

Yet a further aspect of the present disclosure is a method comprising steps of: (a) placing a cadaver bone in a closed container comprising a cryoprotectant solution; (b) reducing the pressure in the closed container, and optionally, holding the closed container at reduced pressure, to remove at least a portion of the water present in the cadaver bone; (c) raising the pressure in the closed container and holding the closed container at a raised pressure to allow infiltration of the cryoprotectant solution into the cadaver bone; (d) removing the cadaver bone from the closed container; (e) chilling the cadaver bone to a temperature at least below 0° C., thereby cryopreserving the cadaver bone; (f) storing the cryopreserved cadaver bone at a temperature at least below 0° C.; (g) transferring the cryopreserved cadaver bone into a grinding medium having a temperature of from about 35° C. to about 45° C. for a time sufficient to warm the cadaver bone fragments to a surface temperature of about 20° C.; (h) grinding warmed cadaver bone fragments to obtain ground cadaver bone; (i) filtering the ground cadaver bone, thereby producing a filtered product comprising bone marrow cells; and (j) collecting the bone marrow cells, thereby obtaining extracted bone marrow cells.

Another aspect of the present disclosure is a method comprising steps of: (a) placing a cadaver bone in a closed container comprising a cryoprotectant solution; (b) reducing the pressure in the closed container, and optionally, holding the closed container at reduced pressure, to remove at least a portion of the water present in the cadaver bone; (c) raising the pressure in the closed container and holding the closed container at a raised pressure to allow infiltration of the cryoprotectant solution into the cadaver bone; (d) removing the cadaver bone from the closed container; (e) chilling the cadaver bone to a temperature at least below 0° C., thereby cryopreserving the cadaver bone; (f) storing the cryopreserved cadaver bone at a temperature at least below 0° C.; (g) transferring the cryopreserved cadaver bone into a grinding medium having a temperature of from about 35° C. to 45° C. for a time sufficient to warm the cadaver bone fragments to a surface temperature of about 20° C.; (h) grinding warmed cadaver bone fragments to obtain ground cadaver bone; (i) filtering the ground cadaver bone, thereby producing a filtered product comprising bone marrow cells and a captured ground bone; (j) collecting the bone marrow cells, thereby obtaining extracted bone marrow cells; and (k) extracting vertebral bone adherent mesenchymal stromal/stem cells (vBA-MSC) from the captured ground bone by contacting the captured ground bone with a digestion solution.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

In any of the above aspects, the method may comprise a step of increasing the pressure in the closed container comprising a cryoprotectant to above 760 mmHg by introducing a compressed gas (e.g., nitrogen, xenon, $CO_2$, argon, $H_2S$, or helium), a gas released by sublimation (e.g., $CO_2$ via dry ice), or a gas provided by evaporation (e.g., nitrogen via liquid nitrogen), thereby permeating gas into the cadaver bone. In embodiments, the gas is $CO_2$, e.g., compressed $CO_2$. In some embodiments, the gas is nitrogen, e.g., compressed nitrogen.

Alternately, in any of the above-mentioned aspects, rather than placing a cadaver bone in a closed container comprising a cryoprotectant solution, the cadaver bone is placed in closed container that lacks a cryoprotectant solution. In these alternate aspects, the method comprises a step of increasing the pressure in the closed container (which lacks a cryoprotectant solution) to above 760 mmHg by introducing a compressed gas (e.g., nitrogen, xenon, $CO_2$, argon, $H_2S$, or helium), a gas released by sublimation (e.g., $CO_2$ via dry ice), or a gas provided by evaporation (e.g., nitrogen via liquid nitrogen), thereby permeating gas into the cadaver bone. Any method disclosed herein may be adapted by comprising initial steps of placing a cadaver bone in closed container that lacks a cryoprotectant solution and increasing the pressure in the closed container to above 760 mmHg by introducing a compressed gas, a gas released by sublimation, or a gas provided by evaporation; in a later step, a cryoprotectant solution is added to the closed container. In embodiments, the gas is $CO_2$, e.g., compressed $CO_2$. In some embodiments, the gas is nitrogen, e.g., compressed nitrogen.

An aspect of the present disclosure is a method for cryopreserving a cadaver bone. The method comprises steps of: (a) placing a cadaver bone in a closed container; (b) increasing the pressure in the closed container to above 760 mmHg by introducing a compressed gas (e.g., nitrogen, xenon, $CO_2$, argon, $H_2S$, or helium), a gas released by sublimation (e.g., $CO_2$ via dry ice), or a gas provided by evaporation (e.g., nitrogen via liquid nitrogen), thereby permeating gas into the cadaver bone; (c) rapidly reducing the pressure in the closed container to no less than 760 mmHg, thereby allowing the gas to expand into the cadaver bone; (d) adding a cryoprotectant solution to the closed container; (e) reducing the pressure in the closed container to below 760 mmHg, optionally, holding the closed container at below 760 mmHg, to remove at least a portion of water and/or at least a portion of the gas present in the cadaver bone; (f) raising the pressure in the closed container and holding the closed container at the raised pressure to allow infiltration of the cryoprotectant solution into the cadaver bone; optionally, slowly adjusting the pressure to about 760 mmHg; (g) removing the cadaver bone from the closed container; and (h) chilling the cadaver bone to a temperature at least below 0° C., thereby cryopreserving the cadaver bone. In this aspect, step (d) precedes step (e) or step (d) follows step (e). In embodiments, the gas is $CO_2$, e.g., compressed $CO_2$. In some embodiments, the gas is nitrogen, e.g., compressed nitrogen.

Another aspect of the present disclosure is a method for cryopreserving a cadaver bone. The method comprises steps of: (a) placing a cadaver bone in a closed container comprising a cryoprotectant solution; (b) increasing the pressure in the closed container to above 760 mmHg by introducing a compressed gas (e.g., nitrogen, xenon, $CO_2$, argon, $H_2S$, or helium), a gas released by sublimination (e.g., $CO_2$ via dry ice), or a gas provided by evaporation (e.g., nitrogen via liquid nitrogen), thereby permeating gas into the cadaver bone; (c) rapidly reducing the pressure in the closed container to no less than 760 mmHg, thereby allowing the gas to expand into the cadaver bone; (d) reducing the pressure in the closed container to below 760 mmHg, optionally, holding the closed container at below 760 mmHg, to remove at least a portion of water and/or at least a portion of the gas present in the cadaver bone; (e) raising the pressure in the closed container and holding the closed container at the raised pressure to allow infiltration of the cryoprotectant solution into the cadaver bone; optionally, slowly adjusting the pressure to about 760 mmHg; (f) removing the cadaver bone from the closed container; and (g) chilling the cadaver bone to a temperature at least below 0° C., thereby cryopreserving the cadaver bone. In embodiments, the gas is $CO_2$, e.g., compressed $CO_2$. In some embodiments, the gas is nitrogen, e.g., compressed nitrogen.

In embodiments of any of the above aspects, a herein disclosed method provides about 1% more viable extracted bone marrow cells to about 100% more viable extracted bone marrow cells, about 101% more viable extracted bone marrow cells to about 200% more viable extracted bone marrow cells, about 2-fold more viable extracted bone marrow cells to about 10-fold more viable extracted bone marrow cells, about 10-fold more viable extracted bone marrow cells to about 100-fold more viable extracted bone marrow cells, about 100-fold more viable extracted bone marrow cells to about 1000-fold more viable extracted bone marrow cells, or about 1000-fold more viable extracted bone marrow cells to about 10000-fold more viable extracted bone marrow cells relative to a method lacking a combination of features as disclosed herein. In some embodiments, the extracted bone marrow cells are hematopoietic stem cells (HSCs; CD34+ cells) and/or mesenchymal stromal/stem cells (MSCs).

Additionally, any method disclosed herein is applicable to any herein-disclosed method. In other words, any aspect or embodiment described herein can be combined with any other aspect or embodiment as disclosed herein.

BRIEF DESCRIPTION OF THE DRAWINGS

This patent application contains at least one drawing executed in color. Copies of this patent or patent application with color drawings will be provided by the Office upon request and payment of the necessary fee.

FIG. 4A, vertebral bodies were subjected to 6 cycles of −500 mm Hg for 10 mins; FIG. 4B, vertebral bodies were subjected to constant −500 mm Hg for 1 hour. These data contrast the vertebral bodies of FIG. 2 that underwent longer incubation period at atmospheric pressure and in which no crystal violet staining is observed to have infiltrated the vertebral bodies.

FIG. 6A shows rates of temperature reduction for bone during the initial chilling stage of the cryopreservation process, which occurs in a static −80° C. freezer. FIG. 6B shows rates of temperature reduction for bone during the subsequent chilling stage of the cryopreservation process, which occurs in liquid nitrogen or in liquid nitrogen vapor.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings.

DETAILED DESCRIPTION

Introduction

Bone marrow is a rich and diverse source of stem and progenitor cells that provide numerous therapeutic and medical research uses. Obtaining bone marrow traditionally has been restricted to aspirating small volumes (~100 ml) from living donors. A vastly more abundant source has been recognized in the form of deceased donor bone marrow; however, the cost and infrastructure required to process and bank even a fraction of eligible donor tissues (>40,000 today) has been prohibitive.

Figure 1:
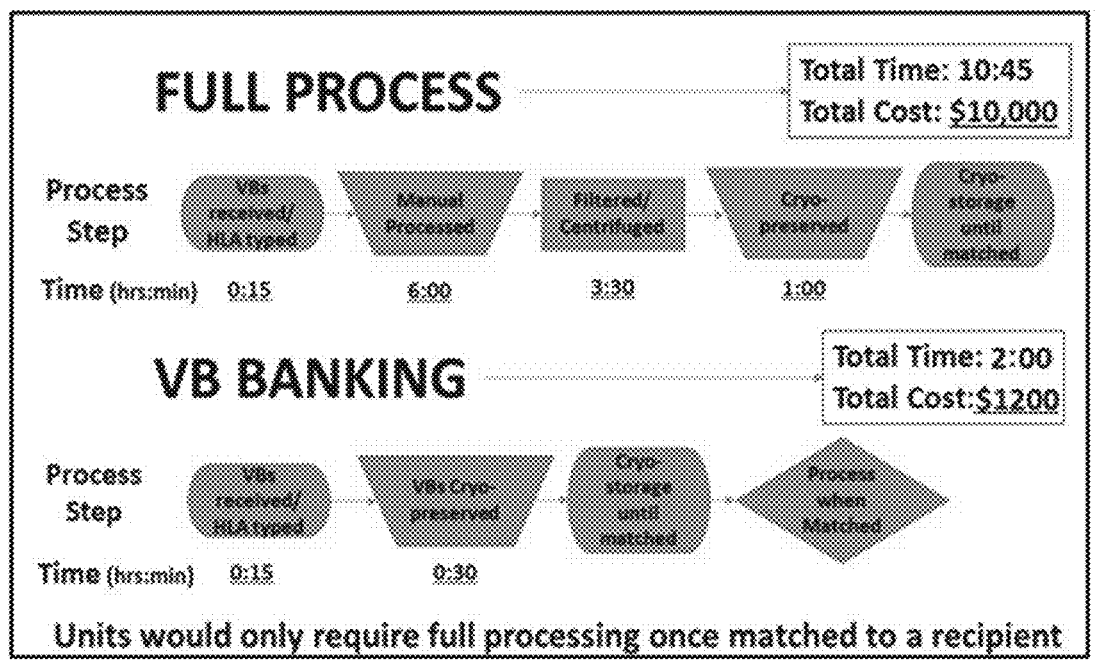
FIG. 1 is a schematic showing time and cost savings through delayed processing of bone marrow according to method of the present disclosure.

Indeed, it currently it costs nearly $10,000 to fully process each cadaver donor specimen (typically 10 vertebral bodies). However, the commercial value of the majority of banked specimens will likely not be realized for many years until the "smart bank" reaches a critical size required for sufficient genetic diversity. As the smart bank grows and rarer human leukocyte antigen (HLA) types are captured, the potential value of the smart bank increases. To minimize up-front costs, the present disclosure implements a "just-in-time" manufacturing model, whereby whole bones (e.g., vertebral bodies) are cryopreserved for subsequent bone marrow extraction, and once a matching recipient is identified. This system allows the "value" of each donor tissue to be assessed before incurring expenses of processing so that resources can be focused on donors satisfying immediate clinical or experimental needs. This innovation minimizes initial costs to 12% of total processing costs (FIG. 1).

This will allow for efficient generation of a large "smart bank" in which units are typed and cryopreserved up front with minimal manipulation and cost to be thawed and processed under GMP conditions upon matching to a recipient.

New method for cryopreserving viable marrow in situ and subsequently recovering viable hematopoietic and mesenchymal stem cells is provided by the present disclosure and as recited in the below appended claims. More specifically, the present disclosure relates to, at least, a vacuum-assisted method for infiltrating cadaver bone with a cryoprotectant and a method for rapidly warming the cryopreserved cadaver bone for bone marrow processing.

Methods for Cryopreserving a Cadaver Bone

An aspect of the present disclosure is a method for cryopreserving a cadaver bone. The method comprises steps of: (a) placing a cadaver bone in a closed container comprising a cryoprotectant solution; (b) reducing the pressure in the closed container, and optionally, holding the closed container at reduced pressure, to remove at least a portion of the water present in the cadaver bone; (c) raising the pressure in the closed container and holding the closed container at a raised pressure to allow infiltration of the cryoprotectant solution into the cadaver bone; (d) removing the cadaver bone from the closed container; and (e) chilling the cadaver bone to a temperature at least below 0° C., thereby cryopreserving the cadaver bone.

Infiltrating Cadaver Bone with a Cryoprotectant

Surprisingly, by immersing a cadaver bone in a closed container of cryoprotectant and applying an intermittent vacuum to the closed container, the cryoprotectant infiltrates the cadaver bone significantly more rapidly that would occur by passive diffusion. Compare FIG. 2 with FIG. 4A and FIG. 4B and FIG. 3 with FIG. 5. Such effective infiltration of cryoprotectant contributes to reduced ice crystal formation during freezing of the cadaver bone and, ultimately, extraction of viable bone marrow cells that have replicative potential.

Steps (b) and (c) may occur only once or steps (b) and (c) may be repeated at least once, at least twice, at least four times, at least five times, or at least six times. In some embodiments, repeating the reduced pressure and the raised pressure may increase infiltration of a cryoprotectant into a cadaver bone. See, e.g., FIG. 5. In other embodiments, there is sufficient infiltration of cryoprotectant into a cadaver bone after a single cycle of reduced pressure and raised pressure.

The reduced pressure in the closed container may any pressure value from about −400 mmHg to about −800 mmHg. The pressure requirement should be sufficient to remove at least a portion of the water present in the cadaver bone. The reduced pressure in the closed container may have a value of about −400 mmHg, −425 mmHg, −450 mmHg, −475 mmHg, −500 mmHg, −525 mmHg, −550 mmHg, −575 mmHg, −600 mmHg, −625 mmHg, −650 mmHg, −675 mmHg, −700 mmHg, −725 mmHg, −750 mmHg, −775 mmHg, or −800 mmHg. In some embodiments, the reduced pressure in the closed container is from about −400 mmHg to about −500 mmHg.

In some embodiments, it takes from about one minute to about 10 minutes for the closed container to reach a desired reduced pressure once the pressure in the closed container begins reducing. As examples, the closed container is may take less than 1 minute, about 1 minute, 2 minutes, 3 minutes, 4 minutes, 5 minutes, 6 minutes, 7 minutes, 8 minutes, 9 minutes, or about 10 minutes and any length of time in between (e.g., a fraction of a minute, e.g., about 5 seconds, 10 seconds, 20 seconds, 30 seconds, 40 seconds, about 50 seconds, and any number of seconds therebetween) to reach the desired reduced pressure. In some embodiments, the cadaver bone reaches the desired reduced pressure rapidly, e.g., from about one second to about one minute.

In some embodiments, the cadaver bone is held at the reduced pressure once the reduced pressure has been reached. The cadaver bone may be held for from less than one minute to about 50 minutes. As examples, the closed container is held at reduced pressure for less than one minute, about 1 minute, 2 minutes, 3 minutes, 4 minutes, 5 minutes, 6 minutes, 7 minutes, 8 minutes, 9 minutes, 10 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 48 minutes, 49 minutes, or about 50 minutes and any length of time in between (e.g., a fraction of a minute, e.g., about 5 seconds, 10 seconds, 20 seconds, 30 seconds, 40 seconds, about 50 seconds, and any number of seconds therebetween). In some embodiments, the cadaver bone is not held at reduced pressure for any measurable time and instead, the method progresses to step (c) of raising the pressure in the closed container.

In step (c), the pressure of the closed container is raised until the pressure is from about 0 mmHg to about 760 mmHg. In other words, the pressure is raised to up to standard atmospheric temperature. The exact raised pressure may be any amount within the specified range, e.g., 0 mmHg, 50 mmHg, 100 mmHg, 150 mmHg, 200 mmHg, 250 mmHg, 300 mmHg, 350 mmHg, 400 mmHg, 450 mmHg, 500 mmHg, 550 mmHg, 600 mmHg, 650 mmHg, 700 mmHg, or 750 mmHg. However, the raised pressure must be high enough to allow infiltration of the cryoprotectant solution into the cadaver bone.

The closed container may be held at the raised pressure for less than about two hours. As examples, for less than one hour, less than one-half hour, about one-half hour, or less time. In some embodiments, the closed container is held at the raised pressure for ten minutes. The duration that the closed container is held at the raised pressure must be long enough to allow infiltration of the cryoprotectant solution into the cadaver bone. As examples, the closed container is held at the raised pressure for about, 1 minute, 2 minutes, 3 minutes, 4 minutes, 5 minutes, 6 minutes, 7 minutes, 8 minutes, 9 minutes, 10 minutes, 21 minutes, 22 minutes, 23 minutes, 24 minutes, 25 minutes, 26 minutes, 27 minutes, 28 minutes, 29 minutes, or about 30 minutes, and any length of time in between (e.g., a fraction of a minute, e.g., about 5 seconds, 10 seconds, 20 seconds, 30 seconds, 40 seconds, about 50 seconds, and any number of seconds therebetween).

The closed container and the cryoprotectant contained therein may be at room temperature. Alternately, the closed container and the cryoprotectant contained therein may be below room temperature, e.g., as low as 4° C. The closed container and the cryoprotectant contained therein may be above room temperature, e.g., as high as 37° C.

Any suitable cryoprotectant may be used in a cryoprotectant solution. Examples of cryoprotectant include dimethyl sulfoxide (also known as DMSO, $C_2H_6OS$, and ME2SO); 1, 2 propane diol (also known as propylene glycol); ethylene glycol; glycerol; foramamide; ethanediol, butane 2,3 diol; hydroxyethyl starch (HES); dextran; sucrose; trehalose; lactose; raffinose; ribotol; mannitol; and polyvinylpyrrolidone (PVP). In some embodiments, the cryoprotectant is DMSO. The cryoprotectant solution may comprise from about 5% DMSO to about 100% DMSO, e.g., about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% DMSO. The cryoprotectant solution may comprise about 20% DMSO. In some embodiments, the cryoprotectant solution may comprise about 40% DMSO or 60% DMSO. In some embodiments, a higher percentage of cryoprotectant is preferred, e.g., percentages that are two times higher than equivalent cell suspension values to help drive osmotic penetration.

The cryoprotectant solution may have water or a saline as base. In some embodiments, the saline is isotonic to human tissues. In embodiments the saline is a 0.9% saline solution. Any commercially available saline solution may be used: sodium chloride solution, PBS, HEPES, Ringers or Lactate. The saline may be 0.9% sodium chloride.

The cryoprotectant solution may further comprise a protein. As examples, the protein may be a human albumin (e.g., HSA) or a constituent of a human platelet lysate. An example of a commercially available human platelet lysate product is Stemulate™ (from Cook® Regentec).

In some embodiments, the cryoprotectant solutions comprises about 10% protein, e.g., 10% human platelet lysate or 10% albumin.

In one example, the cryoprotectant solution comprises about 20% DMSO and about 10% human platelet lysate in 0.9% NaCl.

In another example, the cryoprotectant solution comprises about 40% DMSO and about 10% human platelet lysate in 0.9% NaCl.

In yet another example, the cryoprotectant solution comprises about 60% DMSO and about 10% human platelet lysate in 0.9% NaCl.

In a further example, the cryoprotectant solution comprises about 80% DMSO and about 10% human platelet lysate in 0.9% NaCl.

In an additional example, the cryoprotectant solution comprises about 100% DMSO in 0.9% NaCl.

In any of the above aspects, the method may comprise a step of increasing the pressure in the closed container comprising a cryoprotectant to above 760 mmHg by introducing a compressed gas (e.g., nitrogen, xenon, $CO_2$, argon, $H_2S$, or helium), a gas released by sublimination (e.g., $CO_2$ via dry ice), or a gas provided by evaporation (e.g., nitrogen via liquid nitrogen), thereby permeating gas into the cadaver bone. In embodiments, the gas is $CO_2$, e.g., compressed $CO_2$. In some embodiments, the gas is nitrogen, e.g., compressed nitrogen. The time required for gas infiltration into a vertebral body is less when the gas is compressed versus a gas obtained by sublimination.

Alternately, in any of the above-mentioned aspects, rather than placing a cadaver bone in closed container comprising a cryoprotectant solution, the cadaver bone is placed in a closed container that lacks a cryoprotectant solution. In these alternate aspects, the method comprises a step of increasing the pressure in the closed container (which lacks a cryoprotectant solution) to above 760 mmHg by introducing a compressed gas (e.g., nitrogen, xenon, $CO_2$, argon, $H_2S$, or helium), a gas released by sublimination (e.g., $CO_2$ via dry ice), or a gas provided by evaporation (e.g., nitrogen via liquid nitrogen), thereby permeating gas into the cadaver bone. Any method disclosed herein may be adapted by comprising initial steps of placing a cadaver bone in closed container that lacks a cryoprotectant solution and increasing the pressure in the closed container to above 760 mmHg by introducing a compressed gas, a gas released by sublimination, or a gas provided by evaporation; in a later step, a cryoprotectant solution is added to the closed container. In embodiments, the gas is $CO_2$, e.g., compressed $CO_2$. In some embodiments, the gas is nitrogen, e.g., compressed nitrogen.

Without wishing to be bound by theory, increasing the pressure in a closed container by introducing a compressed gas (e.g., nitrogen, xenon, $CO_2$, argon, $H_2S$, or helium), a gas released by sublimination (e.g., $CO_2$ via dry ice), or a gas provided by evaporation (e.g., nitrogen via liquid nitrogen), promotes infiltration of the cryoprotectant solution into the cadaver bone.

In some cases, the closed container comprises solid materials, e.g., metal, plastic, or other polymers. In some cases, the closed container comprises a foam material, e.g., Styrofoam.

Preparing a Donor Cadaver Bone

In some embodiments, the donor bone is a vertebral body. However, it is understood that the methods described herein can be used on the ilium, a combination of the vertebral bodies and ilium, or other bones suitable for extraction of bone marrow and cells from the marrow, even donor bones with lower expected yields.

The cadaver bone (e.g., vertebral body or iliac crest) to be cryopreserved according to the present disclosure may be substantially intact. In particular, the cadaver bone is not divided into fragments before being placed in a closed container comprising a cryoprotectant solution.

It is understood that the donor bones can be procured according to fixed protocols for clinical recovery. Bones can be recovered by surgeons or by personnel at a trained OPO (organ procurement organization) using an osteotome and mallet from consented organ and tissue donors. Unprocessed bones are preferably wrapped in sponges and towels soaked in saline to ensure moisture retention during hypothermic shipment on wet ice at a temperature of 0 to 10° F. to a processing facility.

The process for preparing the donor bone can occur soon after the bone is obtained from the deceased donor or can occur after the donor bone has been shipped in a hypothermic environment to a processing facility. Since the donor bone can experience prolonged periods of ischemia during recovery and shipment to the processing facility, care must be taken to track the length and type of ischemia.

In some embodiments, the cadaver bone is debrided (i.e., removal of soft tissue) before being placed in a closed container comprising a cryoprotectant solution. The bone may be debrided in an ISO-5 (class 100) environment (biosafety cabinet) with an ISO-7 (class 10,000) background (clean room), with special care taken to sterilize the bag containing the donor bone, such as by spraying with 70% isopropanol. Typically, debriding takes place ex vivo and after harvesting the bone rather than during harvesting the bone. In one embodiment, the debridement is conducted manually using scalpels, osteotomes and gouges. In processing vertebrae, typically a spinal segment including multiple vertebral levels will be provided. In a typical case, a spine segment runs from T8 to L5, for ten vertebral bodies. During initial debridement of the spinal segment, when enough soft tissue has been removed to visualize the pedicles, the pedicles are removed using either a tissue processing band saw or a bone saw, such as the Stryker System 6 Saw (Stryker, Kalamazoo, MI), or with the hand tool shown in FIG. 1A to FIG. 1D of US20200325451A1, the contents of which is incorporated herein by reference in its entirety. Special care is taken to avoid breaching the cortical bone which would expose the cancellous bone, to ensure that the hypoxic cancellous bone marrow remains protected throughout the entire debriding process. The anterior element of the vertebral bodies remains, whereas the pedicles and posterior elements are discarded.

Using a boning knife or tissue processing band saw, the vertebral bodies are separated at the intervertebral discs. The intervertebral disc and soft tissue remaining on each vertebral body is removed with a scalpel, scissors and/or osteotomes, leaving clean, separated vertebral bodies. In the case of donor ilium, the soft tissue can be removed with gouges and a scalpel, with special care again taken to ensure that the cortical bone is not breached. Any anatomical pathologies or injuries of the bone are noted and recorded as part of the batch record for the marrow ultimately obtained from the bones. Bones damaged during the recovery process are discarded.

In some embodiments, the cadaver bone is surface sterilized before being placed in a closed container comprising a cryoprotectant solution. Surface sterilization may comprise contacting the cadaver bone with a bleach solution for at least about 10 minutes to at least about 25 minutes, e.g., about 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, or about 25 minutes. The cadaver bones may be contacted with the bleach solution for longer times, e.g., about 30 minutes, 35 minutes, 40 minutes, 45 minutes, 50 minutes, or longer. Contacting the cadaver bone with a bleach solution for more than 10 minutes yields no significant difference in cell viability compared to when the cadaver bone is soaked for up to 25 minutes. However, without wishing to be bound by theory, an increase in bleaching time improves the ultimate product. For example, increasing the soaking of the cadaver bone in bleach for longer period of time allows the bleach to fill the cavity or crevice of the cadaver bone to further decontaminate or sterilize the cadaver bone.

The bleach solution may be from about 5% bleach to about 15% bleach, e.g., about 5%, 6%, 7%, 8%, 9%, 10%, 11%, 12%, 13%, 14%, or about 15% bleach. Higher amounts of bleach, e.g., 20%, 25%, 30%, 35%, 40%, 45%, or 50% may be used. In some embodiments, the bleach solution comprises about 10% bleach. Contacting the cadaver bone with a bleach solution may comprise submerging the cadaver bone in the bleach solution for a predetermined period, typically 5 or more minutes. Bleach has a broad spectrum of anti-microbial activity, does not leave a toxic residue, is unaffected by water hardness and is fast acting.

Interestingly, bleach treatment provides surface sterilization of the bone, but does not penetrate the bone marrow-containing compartment. Therefore, the bleach treatments disclosed herein do not substantially reduce the yield of viable cells obtained from bone marrow.

After contacting the cadaver bone in the bleach solution, the method may further comprise contacting the cadaver bone with a hydrogen peroxide ($H_2O_2$) solution. The hydrogen peroxide solution may comprise from about 1% hydrogen peroxide to about 5% hydrogen peroxide. In some embodiments, the hydrogen peroxide solution comprises 3% hydrogen peroxide. Most living cells include catalase, which is an enzyme that catalyzes the breakdown of $H_2O_2$ into $H_2O$ and $O_2$. This breakdown manifests as foam or froth when the $H_2O_2$ solution contacts soft tissue but not bone. The foam level can be observed as an indication of the amount of soft tissue remaining on the bone. This observation can be performed manually by a human processor or, in another embodiment, by an automated processor.

In some embodiments, the method further comprises a step of agitating the bleached bone product within the hydrogen peroxide solution. In some embodiments, the submerging the bleached bone product in a solution comprising hydrogen peroxide comprises: submerging the bleached bone product in a container containing the hydrogen peroxide solution; detecting foam or froth associated with the bleached bone product; and repeating the submerging until no foam or froth is detected. In some embodiments, the method further comprises manually removing soft tissue from a bleached bone product that is associated with foam or froth. In some embodiments, an inert contrast dye is added to the solution comprising hydrogen peroxide to enhance visibility of any foam or froth associated with the bleached bone product.

The bleaching step and the hydrogen peroxide steps may be repeated multiple times.

After the surface sterilization, the cadaver bone may be rinsed with water, a saline, or with a cryoprotectant solution. Then the surface sterilized cadaver bone may be placed in a closed container comprising a cryoprotectant solution and the pressure is reduced.

Two-Step Chilling of Cadaver Bone

After the pressure in the closed container comprising the cadaver bone and cryoprotectant solution has been raised and held for a suitable amount of time to allow infiltration of the cryoprotectant solution into the cadaver bone, the cadaver bone, now infiltrated with cryoprotectant, is removed from the closed container.

In some cases, the closed container comprises solid materials, e.g., metal, plastic, or other polymers. In some cases, the closed container comprises a foam material, e.g., Styrofoam.

Figure 6A:
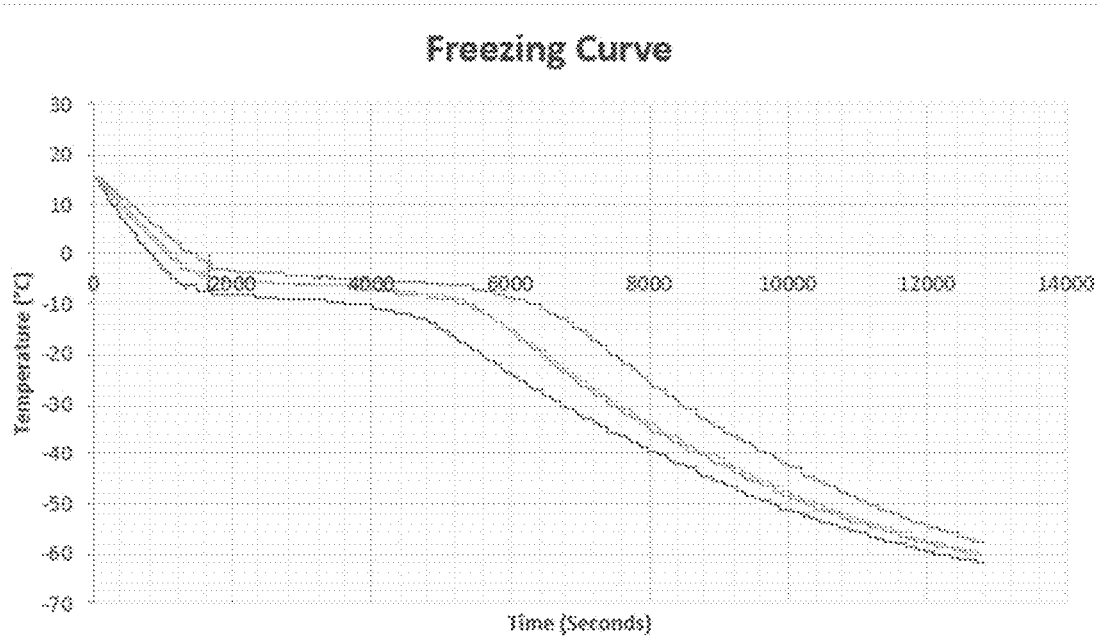
FIG. 6A and FIG. 6B are graphs showing data form the two-stage chilling process for cryopreserving cadaver bone.

The cadaver bone then undergoes an initial chilling period. For this, the cadaver bone is placed in a static minus 80 freezer set at a temperature of colder than about −60° C., e.g., from about −70° C. to about −80° C., or colder than about −100° C. There, the cadaver bone undergoes an initial chilling period. In some embodiments, the cadaver bone is initially chilled in a static minus 80 freezer set at a temperature of about −86° C. Data showing the dynamics of the initial chilling period is shown in FIG. 6A.

In some cases, the static freezer is set at a range of temperature from about −60° C., about −65° C., about −70° C., about −75° C., about −80° C., about −82° C., about −84° C., about −86° C., about −88° C., about −90° C., about −95° C., or about −100° C. In some cases, the freezer can be set at a range of temperature from at least about −60° C., about −65° C., about −70° C., about −75° C., about −80° C., about −82° C., about −84° C., about −86° C., about −88° C., about −90° C., or about −95° C. In some cases, the freezer can be set at a range of temperature from at most about −65° C., about −70° C., about −75° C., about −80° C., about −82° C., about −84° C., about −86° C., about −88° C., about −90° C., about −95° C., or about −100° C.

The cadaver bone may be initially chilled at a rate of from about −0.3° C./min to about −5° C./min. In some embodiments, the cadaver bone is initially chilled at a rate of from about −0.4° C./min to about −0.9° C./min. As examples, the initial chilling rate may be about −0.3° C./min, −0.4° C./min, −0.5° C./min, −0.6° C./min, −0.7° C./min, −0.8° C./min, −0.9° C./min, to about −1° C./min. In other examples, the initial chilling rate may be about −1° C./min, −2° C./min, −3° C./min, −4° C./min, or about −5° C./min. In these rates, the minus sign ("−") means that the temperature is dropping by the stated amount.

The duration of the initial chilling period may vary from a few hours to overnight. The time should be sufficient for the cadaver bone to reach a temperature of colder than about −50° C., e.g., at −60° C. to −80° C. In some embodiments, the bone reaches the desired temperature in about 1 hour, 2 hours, 3 hours, 4 hours, 5 hours, 6 hours, 7 hours, 8 hours, 9 hours, 10 hours, 11 hours, or about 12 hours. Is some embodiments, the cadaver bone is initially chilled in the minus 80 freezer for at least 12 hours or at least overnight.

Without wishing to be bound by theory, it appears that the period of initial chilling in the presence of extracellular ice increases intracellular solute concentrations to an amount that allows intracellular vitrification in the subsequent chilling.

During the period of initial chilling, the cadaver bone is not held in a static freezer having its temperature set to from about −5° C. to about −15° C. and for a period of time from about 1 to about 30 minutes. The cadaver bone may temporarily acquire a temperature of from about −5° C. to about −15° C., but this occurs as the temperature of the cadaver bone is continuously dropping towards the desired temperature, e.g., colder than about −50° C.

Figure 6B:
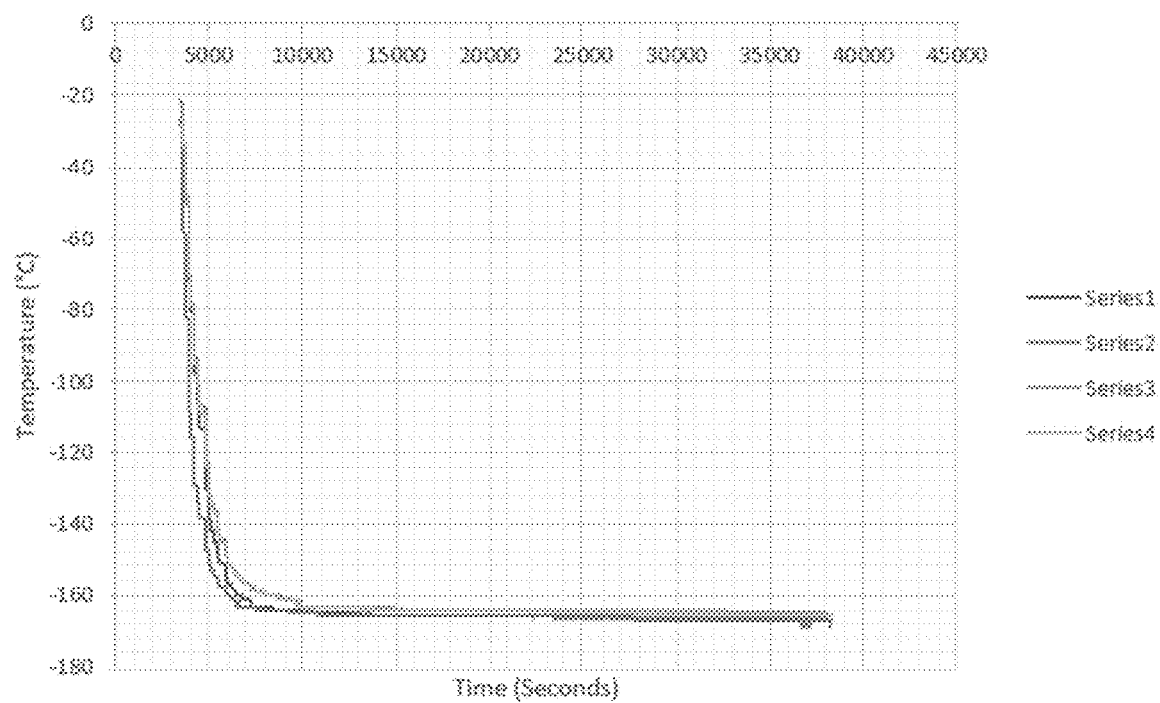

Once the cadaver bone has reached the desired temperature, the cadaver bone undergoes a subsequent chilling period. For this, the cadaver bone is placed in liquid nitrogen or in liquid nitrogen vapor, e.g., at a temperature of about −200° C. Data showing the dynamics of the subsequent chilling period is shown in FIG. 6B. In some embodiments, the subsequent chilling period may occur in a suitable static freezer that is capable of maintaining temperatures equivalent to liquid nitrogen yet without use of liquid nitrogen, e.g., a cryogenic freezer.

During the subsequently chilling period, the cadaver bone is cooled at a rate of from about −2° C./min to about −6° C./min. In some embodiments, the cadaver bone is initially chilled at a rate of about −2° C./min, −2.2° C./min, −2.4° C./min, −2.6° C./min, −2.8° C./min, −3° C./min, −3.2° C./min, −3.4° C./min, −3.6° C./min, −3.8° C./min, −4° C./min, −4.2° C./min, −4.4° C./min, −4.6° C./min, −4.8° C./min, −5° C./min, −5.2° C./min, −5.4° C./min, −5.6° C./min, −5.8° C./min, or about −6° C./min. In these rates, the minus sign ("−") means that the temperature is dropping by the stated amount.

The cryopreserved cadaver bone may be held in liquid nitrogen, in liquid nitrogen vapor, or in a suitable static freezer indefinitely. As examples, the cryopreserved cadaver bone may be held for at least a day, at least a week, at least a month, at least a year, at least five years, or at least 20 years. The cryopreserved cadaver bone may be held in liquid nitrogen, in liquid nitrogen vapor, or suitable static freezer for hundreds or thousands of years.

Without wishing to be bound by theory, the two-step chilling of cadaver bone method, as disclosed herein, improves the viability of the extracted bone marrow cells (hematopoietic stem cells (HSCs; CD34+ cells) and/or mesenchymal stromal/stem cells (MSCs)) relative to methods that do not use the two-step chilling method. Therefore, using the methods of the present disclosure, a greater number of viable cells (HSCs and/or MSCs) are obtained relative to standard methods.

In some cases, the methods of the present disclosure provide from about 1% more viable cells to about 100% more viable cells, e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% more viable cells than from methods that do not use two-step chilling, as disclosed herein.

In some cases, the methods of the present disclosure provide from about 101% more viable cells to about 200% more viable cells, e.g., about 101%, 102%, 103%, 104%, 105%, 106%, 107%, 108%, 109%, 10%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, or about 200% more viable cells than from methods that do not use two-step chilling, as disclosed herein.

In some cases, the methods of the present disclosure provide from about 2-fold more viable cells to about 10-fold more viable cells, e.g., about 2-fold, 3-fold, 4-fold, 5-fold, 6-fold, 7-fold, 8-fold, 9-fold, about 10-fold, or any fold therebetween more viable cells than from methods that do not use two-step chilling, as disclosed herein. As examples, the methods of the present disclosure provide 2-fold to 3-fold, 3-fold to 4-fold, 4-fold to 5-fold, 5-fold to 6-fold, 6-fold to 7-fold, 7-fold to 8-fold, 8-fold to 9-fold, or 9-fold to 10-fold more viable cells than from methods that do not use two-step chilling, as disclosed herein.

In some cases, the methods of the present disclosure provide from about 10-fold more viable cells to about 100-fold more viable cells, e.g., about 10-fold, 20-fold, 30-fold, 40-fold, 50-fold, 60-fold, 70-fold, 80-fold, 90-fold, about 100-fold or any fold therebetween more viable cells than from methods that do not use two-step chilling, as disclosed herein. As examples, the methods of the present disclosure provide 10-fold to 20-fold, 20-fold to 30-fold, 30-fold to 40-fold, 40-fold to 50-fold, 50-fold to 60-fold, 60-fold to 70-fold, 70-fold to 80-fold, 80-fold to 90-fold, or 90-fold to 100-fold more viable cells than from methods that do not use two-step chilling, as disclosed herein.

In some cases, the methods of the present disclosure provide from about 100-fold more viable cells to about 1000-fold more viable cells, e.g., about 100-fold, 200-fold, 300-fold, 400-fold, 500-fold, 600-fold, 700-fold, 800-fold, 900-fold, about 1000-fold or any fold therebetween more viable cells than from methods that do not use two-step chilling, as disclosed herein. As examples, the methods of the present disclosure provide 100-fold to 200-fold, 200-fold to 300-fold, 300-fold to 400-fold, 400-fold to 500-fold, 500-fold to 600-fold, 600-fold to 700-fold, 700-fold to 800-fold, 800-fold to 900-fold, or 900-fold to 1000-fold more viable cells than from methods that do not use two-step chilling, as disclosed herein.

In some cases, the methods of the present disclosure provide from about 1000-fold more viable cells to about 10000-fold more viable cells, e.g., about 1000-fold, 2000-fold, 3000-fold, 4000-fold, 5000-fold, 6000-fold, 7000-fold, 8000-fold, 9000-fold, about 10000-fold or any fold therebetween more viable cells than from methods that do not use two-step chilling, as disclosed herein. As examples, the methods of the present disclosure provide 1000-fold to 200-fold, 2000-fold to 3000-fold, 3000-fold to 4000-fold, 4000-fold to 5000-fold, 5000-fold to 6000-fold, 6000-fold to 7000-fold, 7000-fold to 8000-fold, 8000-fold to 9000-fold, or 9000-fold to 10000-fold more viable cells than from methods that do not use two-step chilling, as disclosed herein.

Methods for Rapidly Warming a Cryopreserved Cadaver Bone

Another aspect of the present disclosure is a method for rapidly warming cadaver bone for providing bone marrow or a derivative thereof. The method comprising steps of: obtaining a cryopreserved cadaver bone; dividing the cryopreserved cadaver bone to obtain fragments of the cryopreserved bone; transferring the fragments of the cryopreserved bone into a grinding medium having a temperature of from about 35° C. to about 45° C. for a time sufficient to warm the cadaver bone fragments to a surface temperature of about 20° C.

In some embodiments, the cryopreserved cadaver bone is cryopreserved by an above-described method, e.g., comprising vacuum-infiltration of a cryoprotectant and/or using a two-step chilling method.

In other embodiments, the cryopreserved cadaver bone is not cryopreserved by an above-described method, e.g., without vacuum-infiltration of a cryoprotectant and/or not using a two-step chilling method.

In some embodiments, a cryopreserved cadaver bone transferred into a grinding medium without having been divided into fragments. Preferably, the cryopreserved cadaver bone has a temperature of at least below 0° C. when transferred into a grinding medium.

In alternate embodiments, the method comprises dividing the cryopreserved cadaver bone to obtain fragments of the cryopreserved bone. Preferably, the cryopreserved cadaver bone has a temperature of below 0° C. when dividing into fragments.

In order to simplify the process and for increased safety to the processing personnel, a custom bone cutting tool as described in US 2019/0343112, which is hereby incorporated by reference in its entirety, is used to divide the cryopreserved cadaver bone into smaller pieces. Another bone cutting tool may be used in combination, or in lieu of the custom bone cutting tool as described in US 2019/0343112.

The elements of the bone cutting tool are formed of medical grade stainless steel. The steel is preferably hardened steel capable of withstanding the forces required to cut through frozen bone. In the cleaning process, the tool is subjected to steam sterilization, which can be deleterious to the steel. Thus, in one feature of the present disclosure, the surfaces of the stainless-steel elements are passivated to prevent oxidation of the steel elements during sterilization.

The manual bone-cutting device for dividing the cryopreserved cadaver bone is capable of generating up to 1000 lbf when less than 50 lbf is applied. Such a manual bone-cutting device comprises: a force transmission mechanism, wherein the force transmission mechanism comprises an elongated force transducing member pivotally coupled to a gear mechanism; and a manually operable handle coupled to an end of the elongated force transducing member, wherein the end is opposite of the gear mechanism. The manual bone-cutting device comprises an upper cutting element and/or a lower cutting element. Its upper cutting element and/or lower cutting element each comprises one or more cutting blades that radiate outwards from a central portion of the upper cutting element and/or the lower cutting element. When the one or more cutting blades divide the cryopreserved cadaver bone into fragments that are generally sector shaped.

The manual bone-cutting device divides the cryopreserved cadaver bone into fragments of the cryopreserved bone. The fragments of the cryopreserved bone are transferred into a grinding medium having a temperature of from about 35° C. to about 45° C. for a time sufficient to warm the cadaver bone fragments to a surface temperature of about 20° C. Alternately, whole cryopreserved bone, which has not been divided, is transferred into a grinding medium having a temperature of from about 35° C. and 45° C. for a time sufficient to warm the cadaver bone fragments to a surface temperature of about 20° C. In some embodiments, the surface temperature of the cadaver bone fragments is higher than 20° C., e.g., 25° C. or higher.

A suitable volume of grinding medium is warmed and held at a temperature of from about 35° C. to about 45° C., for example, by placing a container holding the grinding medium on a hot plate or in a water bath. In some examples, 300 ml, 500 ml or one liter of grinding medium is used to warm the cadaver bone. Preferably, the grinding medium has a temperature of about 37° C. to about 40° C. when the fragments of the cryopreserved bone are transferred to the grinding medium.

Figure 15:
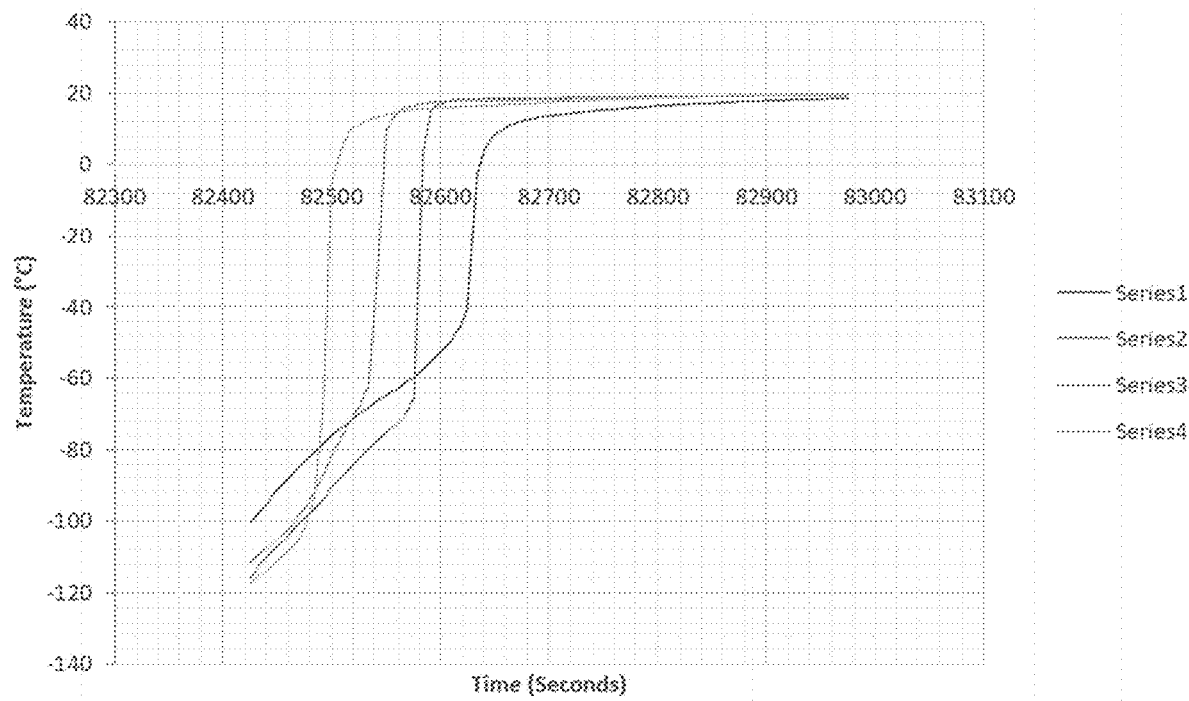
FIG. 15 is a graph showing data from rapid warming of cryopreserved cadaver bone.

The cadaver bone fragments are warmed to a surface temperature of about 20° C. at a rate of from about 100° C./min to about 500° C./min. Is some embodiments, the warming rate is greater than about 300° C./min, e.g., about 300° C./min, 310° C./min, 320° C./min, 330° C./min, 340° C./min, 350° C./min, 360° C./min, 370° C./min, 380° C./min, 390° C./min, 400° C./min, 410° C./min, 420° C./min, 430° C./min, 440° C./min, 450° C./min, 460° C./min, 470° C./min, 480° C./min, 490° C./min, and about 500° C./min. In some embodiments, the warming rate is from about 400° C./min to about 500° C./min. In some instances, the cadaver bone fragments are warmed to a surface temperature of about 20° C. in less than one minute. In some cases, the cadaver bone fragments are warmed to a surface temperature of about 20° C. in about one minute or more, e.g., about 1 minute, 2 minutes, 3 minutes, 4 minutes, 5 minutes, 6 minutes, 7 minutes, 8 minutes, 9 minutes, or about 10 minutes. Data showing the dynamics of the fast warming is shown in FIG. 15.

When whole cadaver bone is warmed in the f2grinding medium, the warming rate will be slower than when bone fragments are warmed. As examples, the cadaver bone is warmed to a surface temperature of about 20° C. at a rate of from about 100° C./min to about 250° C./min.

Without wishing to be bound by theory, the fast warming rate of the present disclosed methods prevents ice recrystallization during thawing of the bone fragments (or whole cadaver bone).

Without wishing to be bound by theory, the rapid warming of cadaver bone method, as disclosed herein, improves the viability of the extracted bone marrow cells (hematopoietic stem cells (HSCs; CD34+ cells) and/or mesenchymal stromal/stem cells (MSCs)) relative to methods that do not use the rapid warming method. Therefore, using the methods of the present disclosure, a greater number of viable cells (HSCs and/or MSCs) are obtained relative to standard methods.

In some cases, the methods of the present disclosure provide from about 1% more viable cells to about 100% more viable cells, e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% more viable cells than from methods that do not use the rapid warming method, as disclosed herein.

In some cases, the methods of the present disclosure provide from about 101% more viable cells to about 200% more viable cells, e.g., about 101%, 102%, 103%, 104%, 105%, 106%, 107%, 108%, 109%, 10%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, or about 200% more viable cells than from methods that do not use the rapid warming method, as disclosed herein.

In some cases, the methods of the present disclosure provide from about 2-fold more viable cells to about 10-fold more viable cells, e.g., about 2-fold, 3-fold, 4-fold, 5-fold, 6-fold, 7-fold, 8-fold, 9-fold, about 10-fold, or any fold therebetween more viable cells than from methods that do not use rapid warming, as disclosed herein. As examples, the methods of the present disclosure provide 2-fold to 3-fold, 3-fold to 4-fold, 4-fold to 5-fold, 5-fold to 6-fold, 6-fold to 7-fold, 7-fold to 8-fold, 8-fold to 9-fold, or 9-fold to 10-fold more viable cells than from methods that do not use rapid warming, as disclosed herein.

In some cases, the methods of the present disclosure provide from about 10-fold more viable cells to about 100-fold more viable cells, e.g., about 10-fold, 20-fold, 30-fold, 40-fold, 50-fold, 60-fold, 70-fold, 80-fold, 90-fold, about 100-fold or any fold therebetween more viable cells than from methods that do not use rapid warming, as disclosed herein. As examples, the methods of the present disclosure provide 10-fold to 20-fold, 20-fold to 30-fold, 30-fold to 40-fold, 40-fold to 50-fold, 50-fold to 60-fold, 60-fold to 70-fold, 70-fold to 80-fold, 80-fold to 90-fold, or 90-fold to 100-fold more viable cells than from methods that do not use rapid warming, as disclosed herein.

In some cases, the methods of the present disclosure provide from about 100-fold more viable cells to about 1000-fold more viable cells, e.g., about 100-fold, 200-fold, 300-fold, 400-fold, 500-fold, 600-fold, 700-fold, 800-fold, 900-fold, about 1000-fold or any fold therebetween more viable cells than from methods that do not use rapid warming, as disclosed herein. As examples, the methods of the present disclosure provide 100-fold to 200-fold, 200-fold to 300-fold, 300-fold to 400-fold, 400-fold to 500-fold, 500-fold to 600-fold, 600-fold to 700-fold, 700-fold to 800-fold, 800-fold to 900-fold, or 900-fold to 1000-fold more viable cells than from methods that do not use rapid warming, as disclosed herein.

In some cases, the methods of the present disclosure provide from about 1000-fold more viable cells to about 10000-fold more viable cells, e.g., about 1000-fold, 2000-fold, 3000-fold, 4000-fold, 5000-fold, 6000-fold, 7000-fold, 8000-fold, 9000-fold, about 10000-fold or any fold therebetween more viable cells than from methods that do not use rapid warming, as disclosed herein. As examples, the methods of the present disclosure provide 1000-fold to 200-fold, 2000-fold to 3000-fold, 3000-fold to 4000-fold, 4000-fold to 5000-fold, 5000-fold to 6000-fold, 6000-fold to 7000-fold, 7000-fold to 8000-fold, 8000-fold to 9000-fold, or 9000-fold to 10000-fold more viable cells than from methods that do not use rapid warming, as disclosed herein.

Grinding Media

In embodiments, the grinding medium comprises two or more of a nuclease, human serum albumin (HSA), heparin, an electrolyte medium, and a growth media. In some cases, the grinding medium comprises three or more of a nuclease, HSA, heparin, an electrolyte medium, and a growth media.

The nuclease may be a DNAse or a nuclease sold under the trademark Benzonase® or Denarase®. Whereas DNase works only on DNA, modern pharmaceutical biotechnology processing relies on enzymes that can cleave both DNA and RNA, and can reduce the viscosity of the solution in which the cells are suspended. Thus, although conventional DNase may be used, preferably, Benzonase® or Denarase® reagent is substituted for DNase.

In some embodiments, the amount of Benzonase® or Denarase® in the grinding media is about 11 U/ml to about 55 U/ml. In some embodiments, the amount of Benzonase in the grinding media is about 11 U/ml to about 15 U/ml, about 11 U/ml to about 20 U/ml, about 11 U/ml to about 25 U/ml, about 11 U/ml to about 30 U/ml, about 11 U/ml to about 35 U/ml, about 11 U/ml to about 40 U/ml, about 11 U/ml to about 45 U/ml, about 11 U/ml to about 50 U/ml, about 11 U/ml to about 55 U/ml, about 15 U/ml to about 20 U/ml, about 15 U/ml to about 25 U/ml, about 15 U/ml to about 30 U/ml, about 15 U/ml to about 35 U/ml, about 15 U/ml to about 40 U/ml, about 15 U/ml to about 45 U/ml, about 15 U/ml to about 50 U/ml, about 15 U/ml to about 55 U/ml, about 20 U/ml to about 25 U/ml, about 20 U/ml to about 30 U/ml, about 20 U/ml to about 35 U/ml, about 20 U/ml to about 40 U/ml, about 20 U/ml to about 45 U/ml, about 20 U/ml to about 50 U/ml, about 20 U/ml to about 55 U/ml, about 25 U/ml to about 30 U/ml, about 25 U/ml to about 35 U/ml, about 25 U/ml to about 40 U/ml, about 25 U/ml to about 45 U/ml, about 25 U/ml to about 50 U/ml, about 25 U/ml to about 55 U/ml, about 30 U/ml to about 35 U/ml, about 30 U/ml to about 40 U/ml, about 30 U/ml to about 45 U/ml, about 30 U/ml to about 50 U/ml, about 30 U/ml to about 55 U/ml, about 35 U/ml to about 40 U/ml, about 35 U/ml to about 45 U/ml, about 35 U/ml to about 50 U/ml, about 35 U/ml to about 55 U/ml, about 40 U/ml to about 45 U/ml, about 40 U/ml to about 50 U/ml, about 40 U/ml to about 55 U/ml, about 45 U/ml to about 50 U/ml, about 45 U/ml to about 55 U/ml, or about 50 U/ml to about 55 U/ml. In some embodiments, the amount of Benzonase in the grinding media is about 11 U/ml, about 15 U/ml, about 20 U/ml, about 25 U/ml, about 30 U/ml, about 35 U/ml, about 40 U/ml, about 45 U/ml, about 50 U/ml, or about 55 U/ml. In some embodiments, the amount of Benzonase in the grinding media is at least about 11 U/ml, about 15 U/ml, about 20 U/ml, about 25 U/ml, about 30 U/ml, about 35 U/ml, about 40 U/ml, about 45 U/ml, or about 50 U/ml. In some embodiments, the amount of Benzonase in the grinding media is at most about 15 U/ml, about 20 U/ml, about 25 U/ml, about 30 U/ml, about 35 U/ml, about 40 U/ml, about 45 U/ml, about 50 U/ml, or about 55 U/ml.

In some embodiments, the amount of Benzonase® in the grinding media is about 1 U/ml to about 10 U/ml. In some embodiments, the amount of Benzonase in the grinding media is about 1 U/ml to about 2 U/ml, about 1 U/ml to about 3 U/ml, about 1 U/ml to about 4 U/ml, about 1 U/ml to about 5 U/ml, about 1 U/ml to about 6 U/ml, about 1 U/ml to about 7 U/ml, about 1 U/ml to about 8 U/ml, about 1 U/ml to about 9 U/ml, about 1 U/ml to about 10 U/ml, about 2 U/ml to about 3 U/ml, about 2 U/ml to about 4 U/ml, about 2 U/ml to about 5 U/ml, about 2 U/ml to about 6 U/ml, about 2 U/ml to about 7 U/ml, about 2 U/ml to about 8 U/ml, about 2 U/ml to about 9 U/ml, about 2 U/ml to about 10 U/ml, about 3 U/ml to about 4 U/ml, about 3 U/ml to about 5 U/ml, about 3 U/ml to about 6 U/ml, about 3 U/ml to about 7 U/ml, about 3 U/ml to about 8 U/ml, about 3 U/ml to about 9 U/ml, about 3 U/ml to about 10 U/ml, about 4 U/ml to about 5 U/ml, about 4 U/ml to about 6 U/ml, about 4 U/ml to about 7 U/ml, about 4 U/ml to about 8 U/ml, about 4 U/ml to about 9 U/ml, about 4 U/ml to about 10 U/ml, about 5 U/ml to about 6 U/ml, about 5 U/ml to about 7 U/ml, about 5 U/ml to about 8 U/ml, about 5 U/ml to about 9 U/ml, about 5 U/ml to about 10 U/ml, about 6 U/ml to about 7 U/ml, about 6 U/ml to about 8 U/ml, about 6 U/ml to about 9 U/ml, about 6 U/ml to about 10 U/ml, about 7 U/ml to about 8 U/ml, about 7 U/ml to about 9 U/ml, about 7 U/ml to about 10 U/ml, about 8 U/ml to about 9 U/ml, about 8 U/ml to about 10 U/ml, or about 9 U/ml to about 10 U/ml. In some embodiments, the amount of Benzonase in the grinding media is about 1 U/ml, about 2 U/ml, about 3 U/ml, about 4 U/ml, about 5 U/ml, about 6 U/ml, about 7 U/ml, about 8 U/ml, about 9 U/ml, or about 10 U/ml. In some embodiments, the amount of Benzonase in the grinding media is at least about 1 U/ml, about 2 U/ml, about 3 U/ml, about 4 U/ml, about 5 U/ml, about 6 U/ml, about 7 U/ml, about 8 U/ml, or about 9 U/ml. In some embodiments, the amount of Benzonase in the grinding media is at most about 2 U/ml, about 3 U/ml, about 4 U/ml, about 5 U/ml, about 6 U/ml, about 7 U/ml, about 8 U/ml, about 9 U/ml, or about 10 U/ml.

It is noted that Denarase® reagent (C-Lecta GmbH) is equivalent to Benzonase® reagent in the same quantity in the present process.

The electrolyte medium in the grinding media may be PLASMALYTE A or ISOLYTE. This electrolyte medium may be the base for the grinding media. PLASMALYTE is a sterile, nonpyrogenic isotonic solution which closely mimics human plasma. It is noted that IMDM (Iscove's Modified Dulbecco's Media) can substitute for the PLASMALYTE™-A, since IMDM is suitable for rapidly proliferating high-density cell cultures and ideal for supporting T- and B-lymphocytes.

In some embodiments, the growth media is Iscove's Modified Dulbecco's Media (IMDM).

The grinding media may comprise heparin. Heparin is used as an anticoagulant. Other anticoagulants at various quantities can also be used. In some embodiments, the amount of heparin in the grinding media is about 5 U/ml to about 15 U/ml. In some embodiments, the amount of heparin in the grinding media is about 5 U/ml to about 6 U/ml, about 5 U/ml to about 7 U/ml, about 5 U/ml to about 8 U/ml, about 5 U/ml to about 9 U/ml, about 5 U/ml to about 10 U/ml, about 5 U/ml to about 11 U/ml, about 5 U/ml to about 12 U/ml, about 5 U/ml to about 13 U/ml, about 5 U/ml to about 14 U/ml, about 5 U/ml to about 15 U/ml, about 6 U/ml to about 7 U/ml, about 6 U/ml to about 8 U/ml, about 6 U/ml to about 9 U/ml, about 6 U/ml to about 10 U/ml, about 6 U/ml to about 11 U/ml, about 6 U/ml to about 12 U/ml, about 6 U/ml to about 13 U/ml, about 6 U/ml to about 14 U/ml, about 6 U/ml to about 15 U/ml, about 7 U/ml to about 8 U/ml, about 7 U/ml to about 9 U/ml, about 7 U/ml to about 10 U/ml, about 7 U/ml to about 11 U/ml, about 7 U/ml to about 12 U/ml, about 7 U/ml to about 13 U/ml, about 7 U/ml to about 14 U/ml, about 7 U/ml to about 15 U/ml, about 8 U/ml to about 9 U/ml, about 8 U/ml to about 10 U/ml, about 8 U/ml to about 11 U/ml, about 8 U/ml to about 12 U/ml, about 8 U/ml to about 13 U/ml, about 8 U/ml to about 14 U/ml, about 8 U/ml to about 15 U/ml, about 9 U/ml to about 10 U/ml, about 9 U/ml to about 11 U/ml, about 9 U/ml to about 12 U/ml, about 9 U/ml to about 13 U/ml, about 9 U/ml to about 14 U/ml, about 9 U/ml to about 15 U/ml, about 10

U/ml to about 11 U/ml, about 10 U/ml to about 12 U/ml, about 10 U/ml to about 13 U/ml, about 10 U/ml to about 14 U/ml, about 10 U/ml to about 15 U/ml, about 11 U/ml to about 12 U/ml, about 11 U/ml to about 13 U/ml, about 11 U/ml to about 14 U/ml, about 11 U/ml to about 15 U/ml, about 12 U/ml to about 13 U/ml, about 12 U/ml to about 14 U/ml, about 12 U/ml to about 15 U/ml, about 13 U/ml to about 14 U/ml, about 13 U/ml to about 15 U/ml, or about 14 U/ml to about 15 U/ml. In some embodiments, the amount of heparin in the grinding media is about 5 U/ml, about 6 U/ml, about 7 U/ml, about 8 U/ml, about 9 U/ml, about 10 U/ml, about 11 U/ml, about 12 U/ml, about 13 U/ml, about 14 U/ml, or about 15 U/ml. In some embodiments, the amount of heparin in the grinding media is at least about 5 U/ml, about 6 U/ml, about 7 U/ml, about 8 U/ml, about 9 U/ml, about 10 U/ml, about 11 U/ml, about 12 U/ml, about 13 U/ml, or about 14 U/ml. In some embodiments, the amount of heparin in the grinding media is at most about 6 U/ml, about 7 U/ml, about 8 U/ml, about 9 U/ml, about 10 U/ml, about 11 U/ml, about 12 U/ml, about 13 U/ml, about 14 U/ml, or about 15 U/ml.

In some embodiments, heparin is omitted from a grinding medium.

The grinding media may comprise human serum albumin (HSA). HSA is a water soluble, monomeric protein that transports hormones, fatty acids and other compounds, buffers pH, and maintains oncotic pressure, among other functions. It is the primary protein present in human blood plasma. HSA provides a protein source to prevent cell adherence and adsorption to surfaces, as well as reactive oxygen scavenging. In some embodiments, HSA is present in the grinding media at about 0.5% to about 5%. In some embodiments, HSA is present in the grinding media at about 0.5% to about 1%, about 0.5% to about 1.5%, about 0.5% to about 2%, about 0.5% to about 2.5%, about 0.5% to about 3%, about 0.5% to about 3.5%, about 0.5% to about 4%, about 0.5% to about 4.5%, about 0.5% to about 5%, about 1% to about 1.5%, about 1% to about 2%, about 1% to about 2.5%, about 1% to about 3%, about 1% to about 3.5%, about 1% to about 4%, about 1% to about 4.5%, about 1% to about 5%, about 1.5% to about 2%, about 1.5% to about 2.5%, about 1.5% to about 3%, about 1.5% to about 3.5%, about 1.5% to about 4%, about 1.5% to about 4.5%, about 1.5% to about 5%, about 2% to about 2.5%, about 2% to about 3%, about 2% to about 3.5%, about 2% to about 4%, about 2% to about 4.5%, about 2% to about 5%, about 2.5% to about 3%, about 2.5% to about 3.5%, about 2.5% to about 4%, about 2.5% to about 4.5%, about 2.5% to about 5%, about 3% to about 3.5%, about 3% to about 4%, about 3% to about 4.5%, about 3% to about 5%, about 3.5% to about 4%, about 3.5% to about 4.5%, about 3.5% to about 5%, about 4% to about 4.5%, about 4% to about 5%, or about 4.5% to about 5%. In some embodiments, HSA is present in the grinding media at about 0.5%, about 1%, about 1.5%, about 2%, about 2.5%, about 3%, about 3.5%, about 4%, about 4.5%, or about 5%. In some embodiments, HSA is present in the grinding media at least about 0.5%, about 1%, about 1.5%, about 2%, about 2.5%, about 3%, about 3.5%, about 4%, or about 4.5%. In some embodiments, HSA is present in the grinding media at most about 1%, about 1.5%, about 2%, about 2.5%, about 3%, about 3.5%, about 4%, about 4.5%, or about 5%.

The grinding medium may comprise Benzonase®, HSA, heparin, and PLASMA-LYTE A.

In some embodiments, the grinding medium comprises PLASMALYTE as a base with 10 U/mL heparin, 2.5% human serum albumin (HSA), and 3 U/mL Benzonase® reagent.

Grinding and Filtering

In some cases, the method further comprises a step of grinding warmed cadaver bone fragments to obtain ground cadaver bone.

An electric bone grinder or a purpose-built bone grinder, such as the grinder of Biorep Technologies Inc, (Miami, FL) can be used in an ISO-5 environment within an ISO-7 clean room. The warmed cadaver bone fragments is kept submerged in grinding media at all times during and after the grinding process. Once all of the warmed cadaver bone fragments are ground, the chamber of the bone grinder is thoroughly rinsed with fresh media. The ground cadaver bone is discharged from the grinder into a vessel containing grinding media, thereby obtaining a ground cadaver bone slurry.

In some embodiments, the ground cadaver bone slurry is mechanically agitated, e.g., via an orbital shaker, to facilitate separation of bone marrow cells from the ground cadaver bone.

In some cases, the ground cadaver bone slurry is mechanically agitated by the shaker at a rate at least about 10 rounds per minute (RPM), 20 RPM, 30 RPM, 40 RPM, 50 RPM, 60 RPM, 70 RPM, 80 RPM, 90 RPM, 100 RPM, 110 RPM, 120 RPM, 130 RPM, 140 RPM, 150 RPM, 160 RPM, 170 RPM, 180 RPM, 190 RPM, 200 RPM, 210 RPM, 220 RPM, 230 RPM, 240 RPM, 250 RPM, or more. In some embodiments, the ground cadaver bone slurry is mechanically agitated for at least 1 minute, 2 minutes, 3 minutes, 4 minutes, 5 minutes, 10 minutes, 15 minutes, 20 minutes, 25 minutes, 30 minutes, or longer. In some embodiments, the mechanical agitation of the ground cadaver bone slurry increases the yield of the bone marrow cells obtained, e.g., by at least about 10%, 20%, 30%, 40%, 50%, 60%, 70%, 80%. 90%, 100%, 2-fold, 3-fold, 4-fold, 5-fold, 10-fold, 20-fold, 50-fold, or more compared to yield of bone marrow cells obtained without the mechanical agitation.

In various embodiments, the method further comprises a step of filtering the ground cadaver bone slurry, thereby producing a filtered product comprising bone marrow cells and a captured ground bone.

In one embodiment, the ground cadaver bone is passed through a series of stainless-steel sieves. In this embodiment, a No. 40 (425 μm) sieve is stacked on top of a No. 80 (177 μm) sieve, which is seated over a catch-pan to receive the liquid filter contents.

The captured ground bone is retained and further processed to obtain vertebral bone adherent mesenchymal stromal/stem cells (vBA-MSCs).

The filtered product may be combined with additional grinding medium, thereby obtaining a diluted bone marrow cell product.

In some embodiments, the diluted bone marrow cell product is further filtered with one or more filters comprising pore sizes ranging from about 200 μm to about 825 μm and/or selected from filters having pore sizes of 200 μm, 500 μm, or 825 μm.

The method may further comprise a step of removing fat from an intermediate product. For example, by placing the diluted bone marrow cell product into a container capable of being centrifuged, centrifuging the container at a speed and duration sufficient to separate out a fat layer, and removing the fat layer from the de-fatted bone marrow cell product or isolating the de-fatted bone marrow cell product from the fat layer.

Additional steps, devices, and systems for grinding cadaver bone fragments to yield bone marrow cell products is described in US20200325451, the entire contents of which is incorporated by reference in its entirety.

Characteristics of Bone Marrow Products

The bone marrow cells extracted from the warmed cadaver bone fragments comprise hematopoietic stem cells (HSCs; CD34+ cells) and mesenchymal stromal/stem cells (MSCs).

In some embodiments, at least about 50% of the extracted bone marrow cells or a derivative thereof are viable, e.g., at least about at least about 70% of the extracted bone marrow cells or a derivative thereof are viable.

In some embodiments, the viability of the extracted bone marrow cells or a derivative thereof is at least about 70% to about 95%. In some embodiments, the viability of the extracted bone marrow cells or a derivative thereof is at least about 70% to about 75%, about 70% to about 80%, about 70% to about 85%, about 70% to about 90%, about 70% to about 95%, about 75% to about 80%, about 75% to about 85%, about 75% to about 90%, about 75% to about 95%, about 80% to about 85%, about 80% to about 90%, about 80% to about 95%, about 85% to about 90%, about 85% to about 95%, or about 90% to about 95%. In some embodiments, the viability of the extracted bone marrow cells or a derivative thereof is at least about 70%, about 75%, about 80%, about 85%, about 90%, or about 95%. In some embodiments, the viability of the extracted bone marrow cells or a derivative thereof is at least at least about 70%, about 75%, about 80%, about 85%, or about 90%. In some embodiments, the viability of the extracted bone marrow cells or a derivative thereof is at least at most about 75%, about 80%, about 85%, about 90%, or about 95%.

The number of the extracted bone marrow cells or a derivative thereof extracted from the warmed cadaver bone fragments is at least about 50% of the number extracted from a fresh cadaver bone. For example, at least about 50%, 52%, 54%, 56%, 58%, 60%, 62%, 64%, 66%, 68%, 70%, 72%, 74%, 76%, 78%, 80%, 82%, 84%, 86%, 88%, or about 90% of the number extracted from a fresh cadaver bone. In some embodiments, the number of the extracted bone marrow cells or a derivative thereof extracted from the warmed cadaver bone fragments is at least about 90% of the number extracted from a fresh cadaver bone.

The number of viable CD34+ cells extracted from the warmed cadaver bone fragments is at least about 70% of the number extracted from a fresh cadaver bone. For example, at least about 70%, 72%, 74%, 76%, 78%, 80%, 82%, 84%, 86%, 88%, or about 90% of the number extracted from a fresh cadaver bone. In some embodiments, the number of viable CD34+ cells extracted from the warmed cadaver bone fragments is at least about 90% of the number extracted from a fresh cadaver bone.

Notably, the number of cells with proliferative potential obtained from the warmed cadaver bone fragments is at least about 50% of the number obtained from a fresh cadaver bone. For example, at least about 50%, 52%, 54%, 56%, 58%, 60%, 62%, 64%, 66%, 68%, 70%, 72%, 74%, 76%, 78%, 80%, 82%, 84%, 86%, 88%, or about 90% of the number extracted from a fresh cadaver bone. In some embodiments, the number of cells with proliferative potential obtained from the warmed cadaver bone fragments is at least about 70% of the number obtained from a fresh cadaver bone.

Without wishing to be bound by theory, vacuum-assisted penetration of a cryoprotectant into whole vertebral bodies, as disclosed herein, improves the viability of the extracted bone marrow cells (hematopoietic stem cells (HSCs; CD34+ cells) and/or mesenchymal stromal/stem cells (MSCs)) relative to methods in which vertebral bodies are only incubated in a cryoprotectant at atmospheric pressure. Therefore, using the methods of the present disclosure, a greater number of viable cells (HSCs and/or MSCs) are obtained relative to only atmospheric incubation in a cryoprotectant.

In some cases, the methods of the present disclosure provide from about 1% more viable cells to about 100% more viable cells, e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% more viable cells than from methods comprising incubation of a cryoprotectant only at atmospheric pressure.

In some cases, the methods of the present disclosure provide from about 101% more viable cells to about 200% more viable cells, e.g., about 101%, 102%, 103%, 104%, 105%, 106%, 107%, 108%, 109%, 10%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, 140%, 141%, 142%, 143%, 144%, 145%, 146%, 147%, 148%, 149%, 150%, 151%, 152%, 153%, 154%, 155%, 156%, 157%, 158%, 159%, 160%, 161%, 162%, 163%, 164%, 165%, 166%, 167%, 168%, 169%, 170%, 171%, 172%, 173%, 174%, 175%, 176%, 177%, 178%, 179%, 180%, 181%, 182%, 183%, 184%, 185%, 186%, 187%, 188%, 189%, 190%, 191%, 192%, 193%, 194%, 195%, 196%, 197%, 198%, 199%, or about 200% more viable cells than from methods comprising incubation of a cryoprotectant only at atmospheric pressure.

In some cases, the methods of the present disclosure provide from about 2-fold more viable cells to about 10-fold more viable cells, e.g., about 2-fold, 3-fold, 4-fold, 5-fold, 6-fold, 7-fold, 8-fold, 9-fold, about 10-fold, or any fold therebetween more viable cells than from methods comprising incubation of a cryoprotectant only at atmospheric pressure. As examples, the methods of the present disclosure provide 2-fold to 3-fold, 3-fold to 4-fold, 4-fold to 5-fold, 5-fold to 6-fold, 6-fold to 7-fold, 7-fold to 8-fold, 8-fold to 9-fold, or 9-fold to 10-fold more viable cells than from methods comprising incubation of a cryoprotectant only at atmospheric pressure.

In some cases, the methods of the present disclosure provide from about 10-fold more viable cells to about 100-fold more viable cells, e.g., about 10-fold, 20-fold, 30-fold, 40-fold, 50-fold, 60-fold, 70-fold, 80-fold, 90-fold, about 100-fold or any fold therebetween more viable cells than from methods comprising incubation of a cryoprotectant only at atmospheric pressure. As examples, the methods of the present disclosure provide 10-fold to 20-fold, 20-fold to 30-fold, 30-fold to 40-fold, 40-fold to 50-fold, 50-fold to 60-fold, 60-fold to 70-fold, 70-fold to 80-fold, 80-fold to 90-fold, or 90-fold to 100-fold more viable cells than from methods comprising incubation of a cryoprotectant only at atmospheric pressure.

In some cases, the methods of the present disclosure provide from about 100-fold more viable cells to about 1000-fold more viable cells, e.g., about 100-fold, 200-fold, 300-fold, 400-fold, 500-fold, 600-fold, 700-fold, 800-fold, 900-fold, about 1000-fold or any fold therebetween more viable cells than from methods comprising incubation of a cryoprotectant only at atmospheric pressure. As examples, the methods of the present disclosure provide 100-fold to 200-fold, 200-fold to 300-fold, 300-fold to 400-fold, 400-fold to 500-fold, 500-fold to 600-fold, 600-fold to 700-fold, 700-fold to 800-fold, 800-fold to 900-fold, or 900-fold to 1000-fold more viable cells than from methods comprising incubation of a cryoprotectant only at atmospheric pressure.

In some cases, the methods of the present disclosure provide from about 1000-fold more viable cells to about 10000-fold more viable cells, e.g., about 1000-fold, 2000-fold, 3000-fold, 4000-fold, 5000-fold, 6000-fold, 7000-fold, 8000-fold, 9000-fold, about 10000-fold or any fold therebetween more viable cells than from methods comprising incubation of a cryoprotectant only at atmospheric pressure. As examples, the methods of the present disclosure provide 1000-fold to 200-fold, 2000-fold to 3000-fold, 3000-fold to 4000-fold, 4000-fold to 5000-fold, 5000-fold to 6000-fold, 6000-fold to 7000-fold, 7000-fold to 8000-fold, 8000-fold to 9000-fold, or 9000-fold to 10000-fold more viable cells than from methods comprising incubation of a cryoprotectant only at atmospheric pressure.

Recovery of MSCs from Processed Bone Marrow

Bone marrow is a well-known source for mesenchymal stromal/stem cells (MSCs) which can be harvested from bone marrow obtained using the methods described above. MSCs are self-renewing, multipotent progenitor cells with multilineage potential to differentiate into cell types of mesodermal origin, such as adipocytes, osteocytes, and chondrocytes. In addition, MSCs can migrate to sites of inflammation and exert potent immunosuppressive and anti-inflammatory effects through interactions between lymphocytes associated with both the innate and adaptive immune system. MSCs can be used in treating osteogenesis imperfect, cartilage defects, myocardial infarction, Crohn's disease, multiple sclerosis, autoimmune disease such as Lupus, liver cirrhosis, osteo arthritis, and rheumatoid arthritis. Matched HSC/MSC units which can be used in co-transplant for treatment of graft vs. host disease (GVHD), and for hematopoietic stem cell transplant support.

The herein-disclosed methods may further comprise a step of extracting vertebral bone adherent mesenchymal stromal/stem cells (vBA-MSCs) from captured ground bone.

The step of extracting of the vBA-MSCs may comprise a step of contacting the captured ground bone with a digestion solution, which comprises one or more distinct enzymes. The one or more distinct enzymes may comprise at least one collagenase and/or at least one neutral protease. The at least one collagenase may comprise collagenase isoforms C1 and C2 at a ratio comprising more collagenase isoform C1 than collagenase isoform C2. The ratio of collagenase isoform C1 to collagenase isoform C2 may about 30 to about 70:about 10 to about 29. The ratio of collagenase isoform C1 to collagenase C2 may be 35:15. In some embodiments, the mass ratio of C1 and C2 for each concentration may be 70:30, 54:46, 37:63, 82:18, 54:46, and 90:10.

In some embodiments, the collagenase concentration is about 0.05 U/ml to about 1.6 U/ml. In some embodiments, the collagenase concentration is about 0.05 U/ml to about 0.1 U/ml, about 0.05 U/ml to about 0.15 U/ml, about 0.05 U/ml to about 0.2 U/ml, about 0.05 U/ml to about 0.25 U/ml, about 0.05 U/ml to about 0.3 U/ml, about 0.05 U/ml to about 0.35 U/ml, about 0.05 U/ml to about 0.4 U/ml, about 0.05 U/ml to about 0.8 U/ml, about 0.05 U/ml to about 1.2 U/ml, about 0.05 U/ml to about 1.6 U/ml, about 0.1 U/ml to about 0.15 U/ml, about 0.1 U/ml to about 0.2 U/ml, about 0.1 U/ml to about 0.25 U/ml, about 0.1 U/ml to about 0.3 U/ml, about 0.1 U/ml to about 0.35 U/ml, about 0.1 U/ml to about 0.4 U/ml, about 0.1 U/ml to about 0.8 U/ml, about 0.1 U/ml to about 1.2 U/ml, about 0.1 U/ml to about 1.6 U/ml, about 0.15 U/ml to about 0.2 U/ml, about 0.15 U/ml to about 0.25 U/ml, about 0.15 U/ml to about 0.3 U/ml, about 0.15 U/ml to about 0.35 U/ml, about 0.15 U/ml to about 0.4 U/ml, about 0.15 U/ml to about 0.8 U/ml, about 0.15 U/ml to about 1.2 U/ml, about 0.15 U/ml to about 1.6 U/ml, about 0.2 U/ml to about 0.25 U/ml, about 0.2 U/ml to about 0.3 U/ml, about 0.2 U/ml to about 0.35 U/ml, about 0.2 U/ml to about 0.4 U/ml, about 0.2 U/ml to about 0.8 U/ml, about 0.2 U/ml to about 1.2 U/ml, about 0.2 U/ml to about 1.6 U/ml, about 0.25 U/ml to about 0.3 U/ml, about 0.25 U/ml to about 0.35 U/ml, about 0.25 U/ml to about 0.4 U/ml, about 0.25 U/ml to about 0.8 U/ml, about 0.25 U/ml to about 1.2 U/ml, about 0.25 U/ml to about 1.6 U/ml, about 0.3 U/ml to about 0.35 U/ml, about 0.3 U/ml to about 0.4 U/ml, about 0.3 U/ml to about 0.8 U/ml, about 0.3 U/ml to about 1.2 U/ml, about 0.3 U/ml to about 1.6 U/ml, about 0.35 U/ml to about 0.4 U/ml, about 0.35 U/ml to about 0.8 U/ml, about 0.35 U/ml to about 1.2 U/ml, about 0.35 U/ml to about 1.6 U/ml, about 0.4 U/ml to about 0.8 U/ml, about 0.4 U/ml to about 1.2 U/ml, about 0.4 U/ml to about 1.6 U/ml, about 0.8 U/ml to about 1.2 U/ml, about 0.8 U/ml to about 1.6 U/ml, or about 1.2 U/ml to about 1.6 U/ml. In some embodiments, the collagenase concentration is about 0.05 U/ml, about 0.1 U/ml, about 0.15 U/ml, about 0.2 U/ml, about 0.25 U/ml, about 0.3 U/ml, about 0.35 U/ml, about 0.4 U/ml, about 0.8 U/ml, about 1.2 U/ml, or about 1.6 U/ml. In some embodiments, the collagenase concentration is at least about 0.05 U/ml, about 0.1 U/ml, about 0.15 U/ml, about 0.2 U/ml, about 0.25 U/ml, about 0.3 U/ml, about 0.35 U/ml, about 0.4 U/ml, about 0.8 U/ml, or about 1.2 U/ml. In some embodiments, the collagenase concentration is at most about 0.1 U/ml, about 0.15 U/ml, about 0.2 U/ml, about 0.25 U/ml, about 0.3 U/ml, about 0.35 U/ml, about 0.4 U/ml, about 0.8 U/ml, about 1.2 U/ml, or about 1.6 U/ml.

In some embodiments, the total collagenase concentrations (C1 and C2 collagenase) are about 25 µg/ml to about 100 µg/ml. In some embodiments, the total collagenase concentrations are about 25 µg/ml to about 32.5 µg/ml, about 25 µg/ml to about 47.5 µg/ml, about 25 µg/ml to about 42.5 µg/ml, about 25 µg/ml to about 50 µg/ml, about 25 µg/ml to about 65 µg/ml, about 25 µg/ml to about 77.5 µg/ml, about 25 µg/ml to about 85 µg/ml, about 25 µg/ml to about 100 µg/ml, about 32.5 µg/ml to about 47.5 µg/ml, about 32.5 µg/ml to about 42.5 µg/ml, about 32.5 µg/ml to about 50 µg/ml, about 32.5 µg/ml to about 65 µg/ml, about 32.5 µg/ml to about 77.5 µg/ml, about 32.5 µg/ml to about 85 µg/ml, about 32.5 µg/ml to about 100 µg/ml, about 47.5 µg/ml to about 42.5 µg/ml, about 47.5 µg/ml to about 50 µg/ml, about 47.5 µg/ml to about 65 µg/ml, about 47.5 µg/ml to about 77.5 µg/ml, about 47.5 µg/ml to about 85 µg/ml, about 47.5 µg/ml to about 100 µg/ml, about 42.5 µg/ml to about 50 µg/ml, about 42.5 µg/ml to about 65 µg/ml, about 42.5 µg/ml to about 77.5 µg/ml, about 42.5 µg/ml to about 85 µg/ml, about 42.5 µg/ml to about 100 µg/ml, about 50 µg/ml to about 65 µg/ml, about 50 µg/ml to about 77.5 µg/ml, about 50 µg/ml to about 85 µg/ml, about 50 µg/ml to about 100 µg/ml, about 65 µg/ml to about 77.5 µg/ml, about 65 µg/ml to about 85 µg/ml, about 65 µg/ml to about 100 µg/ml, about 77.5 µg/ml to about 85 µg/ml, about 77.5 µg/ml to about 100 µg/ml, or about 85 µg/ml to about 100 µg/ml. In some embodiments, the total collagenase concentrations are about 25 µg/ml, about 32.5 µg/ml, about 47.5 µg/ml, about 42.5 µg/ml, about 50 µg/ml, about 65 µg/ml, about 77.5 µg/ml, about 85 µg/ml, or about 100 µg/ml. In some embodiments, the total collagenase concentrations are at least about 25 µg/ml, about 32.5 µg/ml, about 47.5 µg/ml, about 42.5 µg/ml, about 50 µg/ml, about 65 µg/ml, about 77.5 µg/ml, or about 85 µg/ml. In some embodiments, the total collagenase concentrations are at most about 32.5 µg/ml, about 47.5 µg/ml, about 42.5 µg/ml, about 50 µg/ml, about 65 µg/ml, about 77.5 µg/ml, about 85 µg/ml, or about 100 µg/ml.

In accordance with one aspect of the disclosure, neutral protease concentration and collagenase concentrations (C1 and C2 collagenase) and ratio of solution volume (mls) to bone fragment weight (mgs) are determined.

In some embodiments, the neutral protease may be *Paenibacillus polymyxa* neutral protease.

In some embodiments, the digestion solution comprises about 2 U/ml to about 20 U/ml of the neutral protease. In some embodiments, the neutral protease concentration may be about 2 U/ml to about 7 U/ml, about 2 U/ml to about 12 U/ml, about 2 U/ml to about 17 U/ml, about 2 U/ml to about 21 U/ml, about 7 U/ml to about 12 U/ml, about 7 U/ml to about 17 U/ml, about 7 U/ml to about 21 U/ml, about 12 U/ml to about 17 U/ml, about 12 U/ml to about 21 U/ml, or about 17 U/ml to about 21 U/ml. In some embodiments, the neutral protease concentration may be about 2 U/ml, about 7 U/ml, about 12 U/ml, about 17 U/ml, or about 21 U/ml. In some embodiments, the neutral protease concentration may be at least about 2 U/ml, about 7 U/ml, about 12 U/ml, or about 17 U/ml. In some embodiments, the neutral protease concentration may be at most about 7 U/ml, about 12 U/ml, about 17 U/ml, or about 21 U/ml. The digestion solution may comprise the neutral protease at an activity of about 19.6 U/ml.

The volume to weight ration of digestion solution to captured ground bone is about 1:1 to about 15:1, e.g., about 5:1. In some embodiments, the ratio may be 1:1, 2.5:1, 5:1, 7.5:1, 10:1 and 15:1 (volume:weight). In some embodiments, the combination of one or more collagenases and neutral proteases is used to obtain the highest possible yields of vBA-MSC.

In some embodiments, the incubation period is about 1 hour to about 4 hours. In some embodiments, the incubation period is about 1 hour to about 1.5 hours, about 1 hour to about 2 hours, about 1 hour to about 2.5 hours, about 1 hour to about 3 hours, about 1.5 hours to about 2 hours, about 1.5 hours to about 2.5 hours, about 1.5 hours to about 3 hours, about 2 hours to about 2.5 hours, about 2 hours to about 3 hours, or about 2.5 hours to about 3 hours. In some embodiments, the incubation period is about 1 hour, about 1.5 hours, about 2 hours, about 2.5 hours, or about 3 hours. In some embodiments, the incubation period is at least about 1 hour, about 1.5 hours, about 2 hours, or about 2.5 hours. In some embodiments, the incubation period is at most about 1.5 hours, about 2 hours, about 2.5 hours, about 3 hours, or about 4 hours. In some cases, the digestion solution is contacted with the captured ground bone for up to about 4 hours.

In some embodiments, the volume-to-weight ratio was 5:1 at an incubation time of 2.5 hours. In some embodiments, the protease produced neutral protease activity of 19.6 U/ml.

In various embodiments, the digestion solution is contacted with the captured ground bone after the step of collecting bone marrow cells.

In these embodiments, at least about 10 million, at least about 100 million, at least about 1 billion, or at least about 10 billion nucleated cells are extracted from the captured ground bone.

Further details of the MSC recovery process of the present disclosure are found in the technical article in Johnstone et al., "Identification and characterization of a large source of primary mesenchymal stem cells tightly adhered to bone surfaces of human vertebral body marrow cavities." *bioRxiv* 2020.05.04.076950, the entire contents of which is incorporated herein by reference.

Methods for Cryopreserving Cadaver Bone and then Rapidly Warming the Cryopreserved Cadaver Bone Yet another aspect of the present disclosure is a method comprising steps of: (a) placing a cadaver bone in a closed container comprising a cryoprotectant solution; (b) reducing the pressure in the closed container, and optionally, holding the closed container at reduced pressure, to remove at least a portion of the water present in the cadaver bone; (c) raising the pressure in the closed container and holding the closed container at a raised pressure to allow infiltration of the cryoprotectant solution into the cadaver bone; (d) removing the cadaver bone from the closed container; (e) chilling the cadaver bone to a temperature at least below 0° C., thereby cryopreserving the cadaver bone; (f) storing the cryopreserved cadaver bone at a temperature at least below 0° C.; (g) dividing the cryopreserved cadaver bone to obtain fragments of the cryopreserved bone; and (h) transferring the fragments of the cryopreserved bone into a grinding medium having a temperature of from about 35° C. to about 45° C. for a time sufficient to warm the cadaver bone fragments to a surface temperature of about 20° C.

In the above aspect, cryopreserved cadaver bone is divided to obtain fragments of the cryopreserved bone. However, in the below aspect, the cryopreserved cadaver bone is not divided into fragments.

In this aspect, the present disclosure provides a method comprising steps of: (a) placing a cadaver bone in a closed container comprising a cryoprotectant solution; (b) reducing the pressure in the closed container, and optionally, holding the closed container at reduced pressure, to remove at least a portion of the water present in the cadaver bone; (c) raising the pressure in the closed container and holding the closed container at a raised pressure to allow infiltration of the cryoprotectant solution into the cadaver bone; (d) removing the cadaver bone from the closed container; (e) chilling the cadaver bone to a temperature at least below 0° C., thereby cryopreserving the cadaver bone; (f) storing the cryopreserved cadaver bone at a temperature at least below 0° C.; (g) transferring the cryopreserved cadaver bone into a grinding medium having a temperature of from about 35° C. to about 45° C. for a time sufficient to warm the cadaver bone fragments to a surface temperature of about 20° C.

In some cases, the closed container comprises solid materials, e.g., metal, plastic, or other polymers. In some cases, the closed container comprises a foam material, e.g., Styrofoam.

Additional features and embodiments of the immediately above two aspects can be found elsewhere in the present disclosure. Thus, the immediately above two aspects can be combined with any embodiment disclosed herein.

Methods for Cryopreserving Cadaver Bone, Rapidly Warming the Cryopreserved Cadaver Bone, Grinding the Cadaver Bone, and Obtaining Extracted Bone Marrow Cells In an aspect, the present disclosure provides a method comprising steps of: (a) placing a cadaver bone in a closed container comprising a cryoprotectant solution; (b) reducing the pressure in the closed container, and optionally, holding the closed container at reduced pressure, to remove at least a portion of the water present in the cadaver bone; (c) raising the pressure in the closed container and holding the closed container at a raised pressure to allow infiltration of the cryoprotectant solution into the cadaver bone; (d) removing the cadaver bone from the closed container; (e) chilling the cadaver bone to a temperature at least below 0° C., thereby cryopreserving the cadaver bone; (f) storing the cryopreserved cadaver bone at a temperature at least below 0° C.; (g) dividing the cryopreserved cadaver bone to obtain fragments of the cryopreserved bone; (h) transferring the fragments of the cryopreserved bone into a grinding medium having a temperature of from about 35° C. to about 45° C. for a time sufficient to warm the cadaver bone fragments to a surface temperature of about 20° C.; (i) grinding warmed cadaver bone fragments to obtain ground cadaver bone; (j) filtering the ground cadaver bone, thereby producing a filtered product comprising bone marrow cells; and (k) collecting the bone marrow cells, thereby obtaining extracted bone marrow cells.

In the above aspect, cryopreserved cadaver bone is divided to obtain fragments of the cryopreserved bone. However, in the below aspect, the cryopreserved cadaver bone is not divided into fragments.

This aspect of the present disclosure is a method comprising steps of: (a) placing a cadaver bone in a closed container comprising a cryoprotectant solution; (b) reducing the pressure in the closed container, and optionally, holding the closed container at reduced pressure, to remove at least a portion of the water present in the cadaver bone; (c) raising the pressure in the closed container and holding the closed container at a raised pressure to allow infiltration of the cryoprotectant solution into the cadaver bone; (d) removing the cadaver bone from the closed container; (e) chilling the cadaver bone to a temperature at least below 0° C., thereby cryopreserving the cadaver bone; (f) storing the cryopreserved cadaver bone at a temperature at least below 0° C.; (g) transferring the cryopreserved cadaver bone into a grinding medium having a temperature of from about 35° C. to about 45° C. for a time sufficient to warm the cadaver bone fragments to a surface temperature of about 20° C.; (h) grinding warmed cadaver bone fragments to obtain ground cadaver bone; (i) filtering the ground cadaver bone, thereby producing a filtered product comprising bone marrow cells; and (j) collecting the bone marrow cells, thereby obtaining extracted bone marrow cells.

In some cases, the closed container comprises solid materials, e.g., metal, plastic, or other polymers. In some cases, the closed container comprises a foam material, e.g., Styrofoam.

Additional features and embodiments of the immediately above two aspects can be found elsewhere in the present disclosure. Thus, the immediately above two aspects can be combined with any embodiment disclosed herein.

Methods for Cryopreserving Cadaver Bone, Rapidly Warming the Cryopreserved Cadaver Bone, Grinding the Cadaver Bone, Obtaining Extracted Bone Marrow Cells, and Extracting Vertebral Bone Adherent Mesenchymal Stromal/Stem Cells (vBA-MSC)

In another aspect, the present disclosure provides a method comprising steps of: (a) placing a cadaver bone in a closed container comprising a cryoprotectant solution; (b) reducing the pressure in the closed container, and optionally, holding the closed container at reduced pressure, to remove at least a portion of the water present in the cadaver bone; (c) raising the pressure in the closed container and holding the closed container at a raised pressure to allow infiltration of the cryoprotectant solution into the cadaver bone; (d) removing the cadaver bone from the closed container; (e) chilling the cadaver bone to a temperature at least below 0° C., thereby cryopreserving the cadaver bone; (f) storing the cryopreserved cadaver bone at a temperature at least below 0° C.; (g) dividing the cryopreserved cadaver bone to obtain fragments of the cryopreserved bone; (h) transferring the fragments of the cryopreserved bone into a grinding medium having a temperature of from about 35° C. to about 45° C. for a time sufficient to warm the cadaver bone fragments to a surface temperature of about 20° C.; (i) grinding warmed cadaver bone fragments to obtain ground cadaver bone; (j) filtering the ground cadaver bone, thereby producing a filtered product comprising bone marrow cells and a captured ground bone; (k) collecting the bone marrow cells, thereby obtaining extracted bone marrow cells; and (l) extracting vertebral bone adherent mesenchymal stromal/stem cells (vBA-MSC) from the captured ground bone by contacting the captured ground bone with a digestion solution.

In the above aspect, cryopreserved cadaver bone is divided to obtain fragments of the cryopreserved bone. However, in the below aspect, the cryopreserved cadaver bone is not divided into fragments.

This aspect of the present disclosure is a method comprising steps of: (a) placing a cadaver bone in a closed container comprising a cryoprotectant solution; (b) reducing the pressure in the closed container, and optionally, holding the closed container at reduced pressure, to remove at least a portion of the water present in the cadaver bone; (c) raising the pressure in the closed container and holding the closed container at a raised pressure to allow infiltration of the cryoprotectant solution into the cadaver bone; (d) removing the cadaver bone from the closed container; (e) chilling the cadaver bone to a temperature at least below 0° C., thereby cryopreserving the cadaver bone; (f) storing the cryopreserved cadaver bone at a temperature at least below 0° C.; (g) transferring the cryopreserved cadaver bone into a grinding medium having a temperature of from about 35° C. to about 45° C. for a time sufficient to warm the cadaver bone fragments to a surface temperature of about 20° C.; (h) grinding warmed cadaver bone fragments to obtain ground cadaver bone; (i) filtering the ground cadaver bone, thereby producing a filtered product comprising bone marrow cells and a captured ground bone; (j) collecting the bone marrow cells, thereby obtaining extracted bone marrow cells; and (k) extracting vertebral bone adherent mesenchymal stromal/stem cells (vBA-MSC) from the captured ground bone by contacting the captured ground bone with a digestion solution.

In some cases, the closed container comprises solid materials, e.g., metal, plastic, or other polymers. In some cases, the closed container comprises a foam material, e.g., Styrofoam.

Additional features and embodiments of the immediately above two aspects can be found elsewhere in the present disclosure. Thus, the immediately above two aspects can be combined with any embodiment disclosed herein.

Methods for Cryopreserving Cadaver Bone Comprising a Step of Raising the Pressure in a Closed Container Lacking a Cryoprotectant Solution In an aspect, the present disclosure provides a method comprising steps of: (a) placing a cadaver bone in a closed container; (b) increasing the pressure in the closed container to above 760 mmHg by introducing a compressed gas (e.g., nitrogen, xenon, $CO_2$, argon, $H_2S$, or helium), a gas released by sublimination (e.g., $CO_2$ via dry ice), or a gas provided by evaporation (e.g., nitrogen via liquid nitrogen), thereby permeating gas into the cadaver bone; (c) rapidly reducing the pressure in the closed container to no less than 760 mmHg, thereby allowing the gas to expand into the cadaver bone; (d) adding a cryoprotectant solution to the closed container; (e) reducing the pressure in the closed container to below 760 mmHg, optionally, holding the closed container at below 760 mmHg, to remove at least a portion of water and/or at least a portion of the gas present in the cadaver bone; (f) raising the pressure in the closed container and holding the closed container at the raised pressure to allow infiltration of the cryoprotectant solution into the cadaver bone; optionally, slowly adjusting the pressure to about 760 mmHg; (g) removing the cadaver bone from the closed container; and (h) chilling the cadaver bone to a temperature at least below 0° C., thereby cryopreserving the cadaver bone. In this aspect, step (d) precedes step (e) or step (d) follows step (e). In embodiments, the gas is $CO_2$, e.g., compressed $CO_2$. In some embodiments, the gas is nitrogen, e.g., compressed nitrogen.

In some cases, the closed container comprises solid materials, e.g., metal, plastic, or other polymers. In some cases, the closed container comprises a foam material, e.g., Styrofoam. When liquid nitrogen is used to provide nitrogen by evaporation, liquid nitrogen may be added to the closed container (e.g., a Styrofoam cooler) and the container reversibly sealed (e.g., using cling film). When dry ice is used to provide $CO_2$ by sublimination, blocks of dry ice may be added to the closed container (e.g., a Styrofoam cooler) and the container reversibly sealed (e.g., using cling film). The time required for gas infiltration into a vertebral body is longer when a gas obtained by sublimination versus the gas being compressed.

Additional features and embodiments of the immediately above aspect can be found elsewhere in the present disclosure. Thus, the immediately above aspect can be combined with any embodiment disclosed herein.

Methods for Cryopreserving Cadaver Bone Comprising a Step of Raising the Pressure in a Closed Container Comprising a Cryoprotectant Solution In another aspect, the present disclosure provides a method comprising steps of: (a) placing a cadaver bone in a closed container comprising a cryoprotectant solution; (b) increasing the pressure in the closed container to above 760 mmHg by introducing a compressed gas (e.g., nitrogen, xenon, $CO_2$, argon, $H_2S$, or helium), a gas released by sublimination (e.g., $CO_2$ via dry ice), or a gas provided by evaporation (e.g., nitrogen via liquid nitrogen), thereby permeating gas into the cadaver bone; (c) rapidly reducing the pressure in the closed container to no less than 760 mmHg, thereby allowing the gas to expand into the cadaver bone; (d) reducing the pressure in the closed container to below 760 mmHg, optionally, holding the closed container at below 760 mmHg, to remove at least a portion of water and/or at least a portion of the gas present in the cadaver bone; (e) raising the pressure in the closed container and holding the closed container at the raised pressure to allow infiltration of the cryoprotectant solution into the cadaver bone; optionally, slowly adjusting the pressure to about 760 mmHg; (f) removing the cadaver bone from the closed container; and (g) chilling the cadaver bone to a temperature at least below 0° C., thereby cryopreserving the cadaver bone. In embodiments, the gas is $CO_2$, e.g., compressed $CO_2$. In some embodiments, the gas is nitrogen, e.g., compressed nitrogen.

In some cases, the closed container comprises solid materials, e.g., metal, plastic, or other polymers. In some cases, the closed container comprises a foam material, e.g., Styrofoam. When liquid nitrogen is used to provide nitrogen by evaporation, liquid nitrogen may be added to the closed container (e.g., a Styrofoam cooler) and the container reversibly sealed (e.g., using cling film). When dry ice is used to provide $CO_2$ by sublimination, blocks of dry ice may be added to the closed container (e.g., a Styrofoam cooler) and the container reversibly sealed (e.g., using cling film). The time required for gas infiltration into a vertebral body is longer when a gas obtained by sublimination versus the gas being compressed.

Additional features and embodiments of the immediately above aspect can be found elsewhere in the present disclosure. Thus, the immediately above aspect can be combined with any embodiment disclosed herein.

Definitions

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Use of absolute or sequential terms, for example, "will," "will not," "shall," "shall not," "must," "must not," "first," "initially," "next," "subsequently," "before," "after," "lastly," and "finally," are not meant to limit scope of the present embodiments disclosed herein but as exemplary.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

As used herein, "or" may refer to "and", "or," or "and/or" and may be used both exclusively and inclusively. For example, the term "A or B" may refer to "A or B", "A but not B", "B but not A", and "A and B". In some cases, context may dictate a particular meaning.

Any systems, methods, software, and platforms described herein are modular. Accordingly, terms such as "first" and "second" do not necessarily imply priority, order of importance, or order of acts.

The term "about" when referring to a number or a numerical range means that the number or numerical range referred to is an approximation within experimental variability (or within statistical experimental error), and the number or numerical range may vary from, for example, from 1% to 15% of the stated number or numerical range. In examples, the term "about" refers to ±10% of a stated number or value. In some instances, the term "about" refers to one standard deviation greater or less than the stated number or value.

The term "from" as in "from 1 to 10" includes the initial and final number recited. Therefore, "from 1 to 10" includes the whole numbers 1, 2, 3, 4, 5, 6, 7, 8, 9, and 10 and includes fractions thereof, (e.g., about 0.1, 0.2, 0.3, 0.4, 0.5, 0.6, 0.7, 0.8, and about 0.9).

The terms "increased", "increasing", or "increase" are used herein to generally mean an increase by a statically significant amount. In some aspects, the terms "increased," or "increase," mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase from about 10 to about 100% as compared to a reference level, standard, or control. Other examples of "increase" include an increase of at least 2-fold, at least 5-fold, at least 10-fold, at least 20-fold, at least 50-fold, at least 100-fold, at least 1000-fold or more as compared to a reference level.

The terms "decreased", "decreasing", or "decrease" are used herein generally to mean a decrease by a statistically significant amount. In some aspects, "decreased" or "decrease" means a reduction by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease from about 10 to about 100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

CD34: Antigen present on immature hematopoietic precursor cells and all hematopoietic colony-forming cells in bone marrow and blood. Certain populations of non-hematopoietic (i.e., CD45 negative) cells also express CD34. Of hematopoietic (i.e., CD45+ cells), the CD34 antigen expression is highest on early progenitor cells and decreases with the maturation of cells. The CD34 antigen is absent on fully differentiated hematopoietic cells. Normal peripheral blood lymphocytes, monocytes, granulocytes, and platelets do not express the CD34 antigen.

Preferably, a gas used in methods of the present disclosure is generally recognized as non-harmful to human cells. In some embodiment, the gas is an inert gas, which is a gas that does not undergo chemical reactions under a set of given conditions. The group 18 elements (including helium, neon, argon, krypton, xenon, and radon) are commonly known as noble gases and also referred to as inert gases. As used herein, nitrogen and argon are considered inert gas. Inert gases are used generally to avoid unwanted chemical reactions degrading a sample. These undesirable chemical reactions are often oxidation and hydrolysis reactions with the oxygen and moisture in air. The term inert gas is context-dependent because several of them can be made to react under certain conditions. Other gases useful in methods of the present disclosure include $CO_2$ and $H_2S$. The gas may be introduced as a compressed gas (e.g., nitrogen, xenon, $CO_2$, argon, $H_2S$, or helium), as a gas released by sublimation (e.g., $CO_2$ via dry ice), or as a gas provided by evaporation (e.g., nitrogen via liquid nitrogen).

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

EXAMPLES

The following illustrative examples are representative of embodiments of the methods disclosed herein and are not meant to be limiting in any way.

Example 1: Illustrative Methods for Cryopreserving Cadaver Bone

In this example, a cadaver bone was infiltrated with a cryoprotectant by use of reduced pressure (i.e., vacuum assisted infiltration of cryoprotectant).

A cadaver bone for extraction of bone marrow was obtained. In this example, the cadaver bone was a vertebral body. The cadaver bone was mechanically debrided and surface sterilized with a bleach solution (e.g., from about 5% to about 15% bleach) followed by incubation in a hydrogen peroxide solution of from about 1% to about 5% hydrogen peroxide.

The cadaver bone was placed in a closed container comprising a cryoprotectant solution. The closed container was capable of reducing the pressure to below atmospheric pressure, i.e., it was capable of creating a low pressure (e.g., vacuum conditions) within the closed container.

In some cases, the closed container comprises solid materials, e.g., metal, plastic, or other polymers. In some cases, the closed container comprises a foam material, e.g., Styrofoam.

The cryoprotectant solution comprised about 20% DMSO and about 10% human platelet lysate in 0.9% NaCl. However, the DMSO concentration could be any amount sufficient to cryoprotect a bone and, importantly, preserve viability of the cells contained therein. As examples, the DMSO concentration may be 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% DMSO. Also, other cryoprotectants disclosed herein (i.e., 1,2 propane diol (also known as propylene glycol); ethylene glycol; glycerol; foramamide; ethanediol, or butane 2,3 diol; hydroxyethyl starch (HES); dextran; sucrose; trehalose; lactose; raffinose; ribotol; mannitol; and polyvinylpyrrolidone (PVP) could be used and at concentrations sufficient to preserve viability of the cells contained within a bone.

The pressure in the closed container was reduced to below atmospheric, e.g., from about −400 mmHg to about −500 mmHg. In some instances, the closed container was held at the reduced pressure for a period of time. In other instances, once the desired reduced pressure has been achieved, the pressure was released to raise back to about atmospheric. The reduced pressure removed at least a portion of the water present in the cadaver bone.

When the pressure in the closed container was raised (up to about atmospheric pressure), the cryoprotectant infiltrated, at least, into the spaces in the cadaver bone vacated by the removed water. The cadaver bone was held at the raised pressure for a time period sufficient to allow infiltration of the cryoprotectant solution into the cadaver bone, e.g., ten minutes up to an hour or a few hours.

In some cases, the reducing pressure and raising pressure was repeated multiple times. See, FIG. 5 which illustrates a protocol in which the pressure was reduced and raised multiple times.

Figure 2:
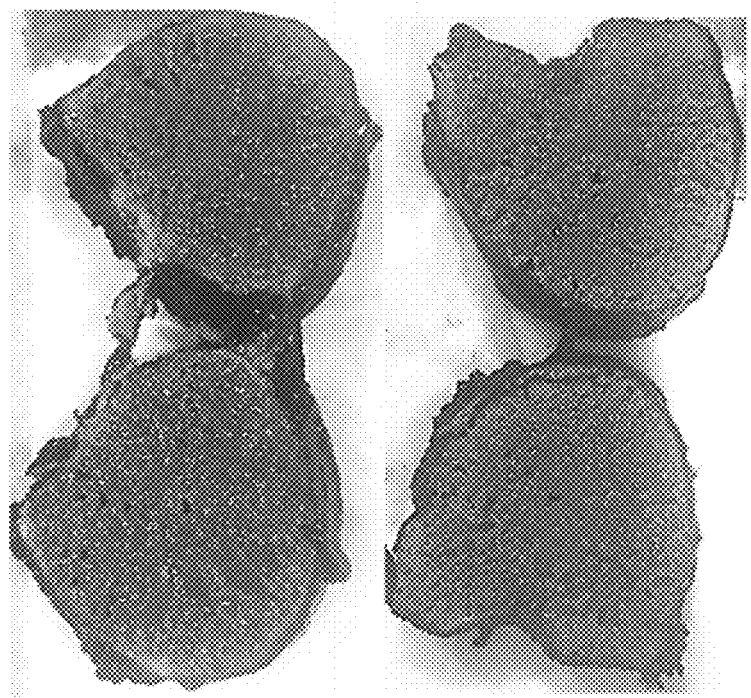
FIG. 2 is a photograph showing crystal violet staining of cancellous bone in intact vertebral bodies after incubating at atmospheric pressure for one day (left) or three days (right). Virtually no crystal violet staining is observed to have infiltrated the vertebral bodies.
Figure 3:
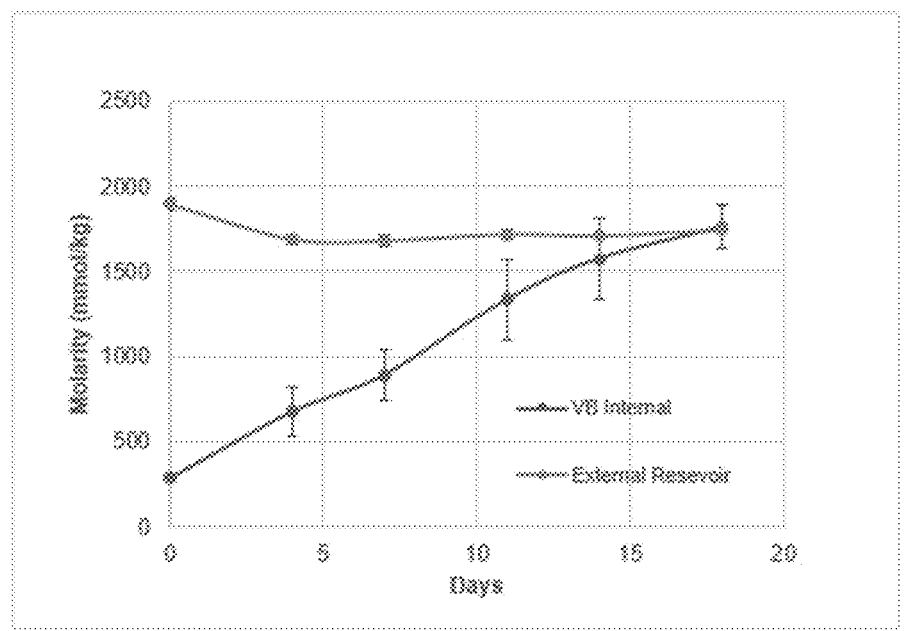
FIG. 3 is a graph showing very slow penetration, at atmospheric pressure, of DMSO into interior of whole vertebral bodies as measured with an osmometer by taking samples from port formed in the vertebral bodies.
Figure 4A:
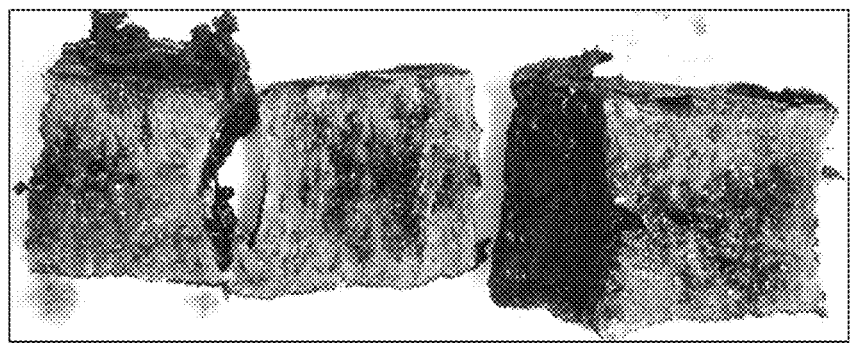
FIG. 4A and FIG. 4B are photographs showing enhanced infiltration of crystal violet dye via vacuum-assistance.
Figure 4B:
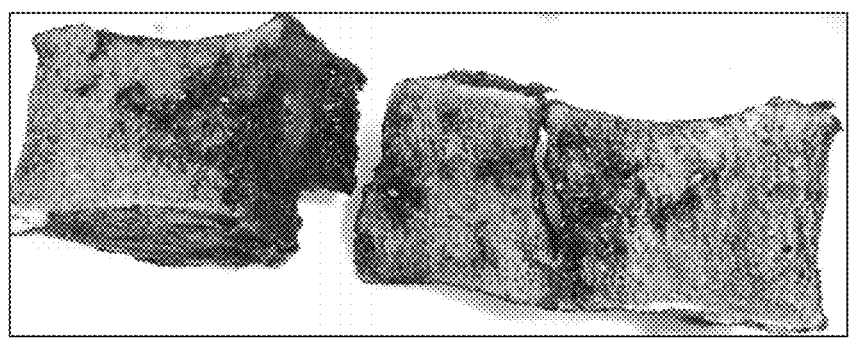
Figure 5:
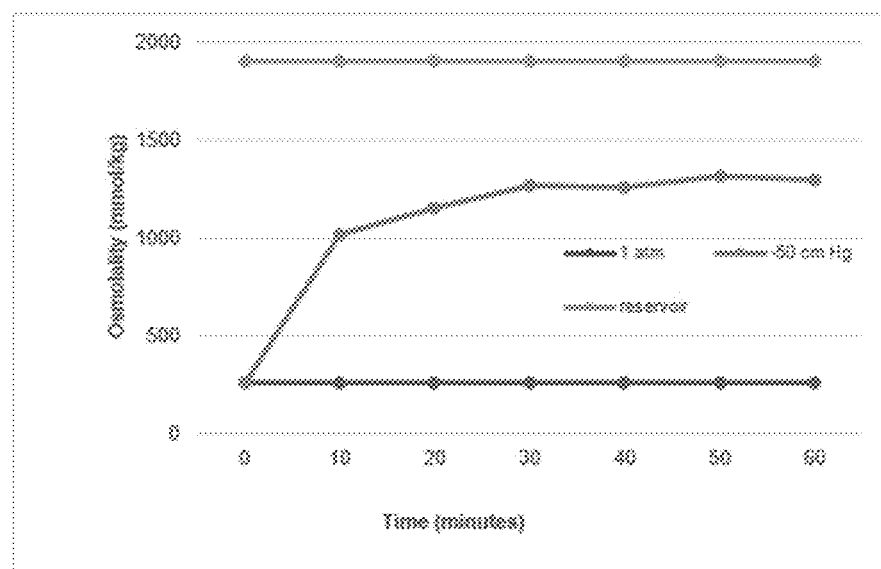
FIG. 5 shows data from vacuum-assisted penetration of a cryoprotectant into whole vertebral bodies. Vertebral bodies were covered with a solution of 20% DMSO in PLASMA-LYTE. One set was left at atmospheric pressure (bottom, blue data). The other was placed under a −500 mm Hg vacuum for 10 minutes, repeated by 5 more cycles (middle, red data). Osmolality of interior vertebral bodies was measured at each 10 min. interval through a sampling port in the endcap. The exterior CPA reservoir osmolarity was also sampled (top, green data).

As shown in FIG. 4A and FIG. 4B, the reduced pressure followed by raised pressure method was effective in promoting infiltration of an external solution into cadaver bone, whereas, as shown in FIG. 2, passive diffusion, even for extended periods of time is not effective. See also FIG. 3 and FIG. 5 which quantify data described in this example.

Once the cadaver bone had been sufficiently infiltrated with cryoprotectant, it was removed from the closed container and placed in a minus 80 freezer, preferably set for −86° C. Over the course of twelve hours to overnight, the cadaver bone underwent an initial chilling period. The change in temperature of cadaver bone during the initial chilling period is shown in FIG. 6A.

Then, the cadaver bone was transferred into a chamber containing liquid nitrogen and/or liquid nitrogen vapor to undergo a subsequent chilling period. The change in temperature of cadaver bone during the subsequent chilling period is shown in FIG. 6B.

Once the cadaver bone has reached the ideal temperature, the bone could remain stored in cold storage indefinitely.

Figure 7:
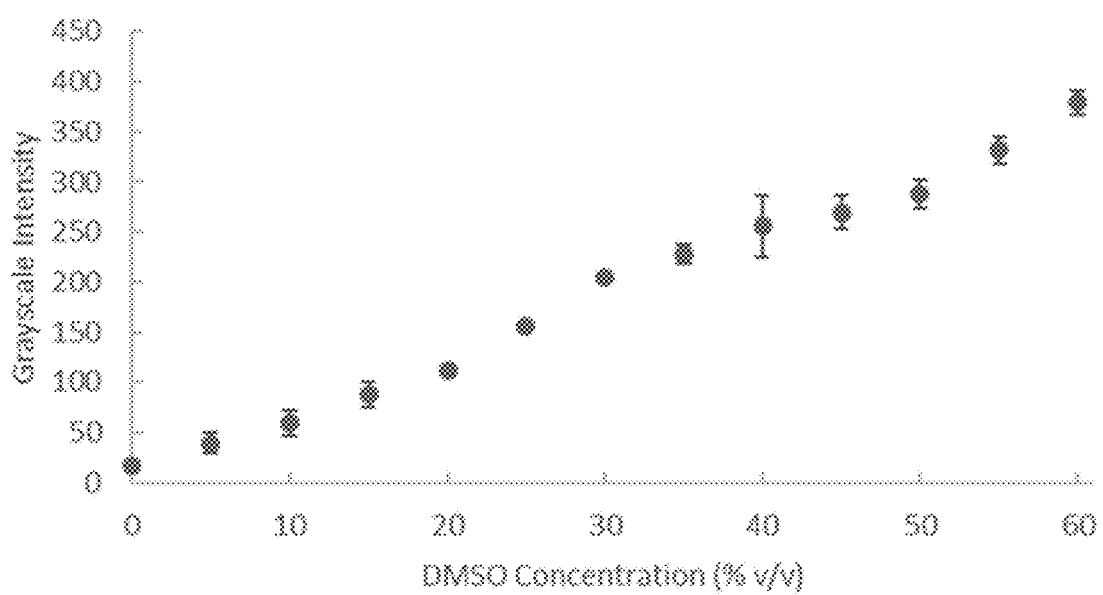
FIG. 7 is a graph showing measured grayscale intensity for DMSO solutions ranging from 0 to 60% v/v for generating a standard curve to estimate cryoprotectant infiltration. Error bars represent SD (n=3)
Figure 8:
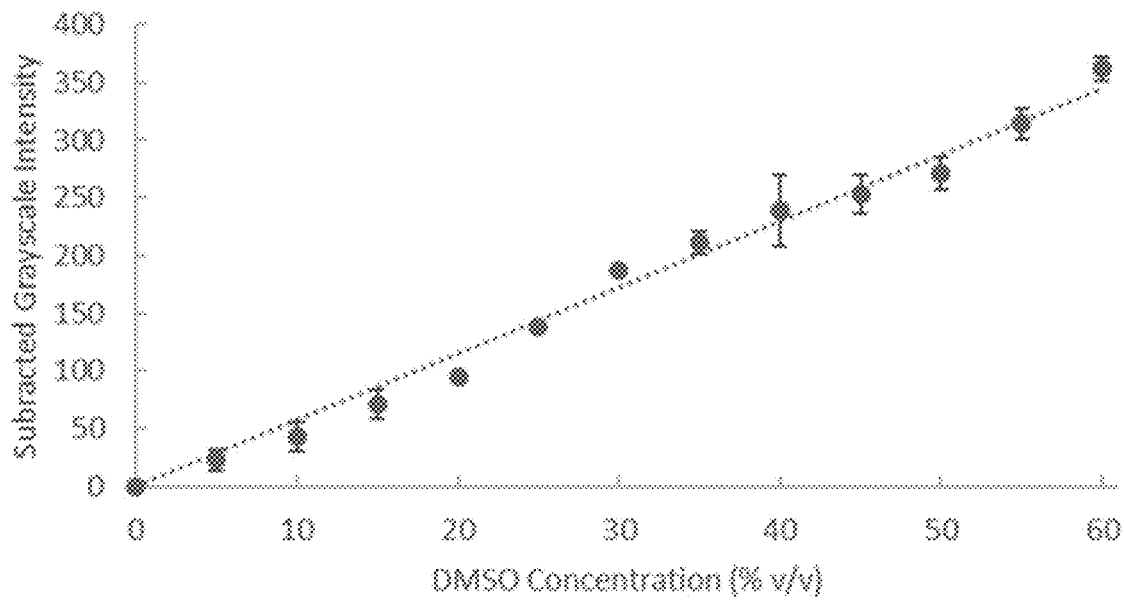
FIG. 8 is a graph showing grayscale intensity for DMSO solutions (of FIG. 7) after subtracting the intensity of 0% DMSO. The dotted line indicates the fitted linear model. The coefficient of determination showed good agreement between the model and data ($R^2$=0.996). Error bars represent SD (n=3).

Amounts of infiltrated cryoprotectant, e.g., DMSO, can be estimated using imaging techniques and comparted to standard curves derived from various concentrations of DMSO. To generate a DMSO Solution Standard Curve a range of DMSO concentrations from 0-60% v/v with 5% intervals were made in triplicate and added to 24-well plates. The DMSO solutions were imaged. For each well, a single, volume-averaged grayscale intensity was measured (FIG. 7). The intensity of 0% DMSO was subtracted from each to give the expected intensity increase of DMSO solutions over water (FIG. 8). In FIG. 8, the dotted line indicates the fitted linear model. The coefficient of determination showed good agreement between the model and data ($R2=0.996$). To convert between an increase in grayscale intensity and DMSO concentration (present in a treated vertebral body), a linear model was fitted to the subtracted grayscale intensity, resulting in a conversion factor of 5.75 intensity units per 1% DMSO; thereby providing the following equation $$\Delta \text{Intensity} = 5.75 * \text{DMSO Concentration} * \text{Porosity},$$

with the porosity accounting for the exchangeable fluid fraction available in a vertebral body. Based on this equation, for a given volume of water, if it were replaced with 20% DMSO, an increase in grayscale intensity of 115 would be expected.

Figure 9:
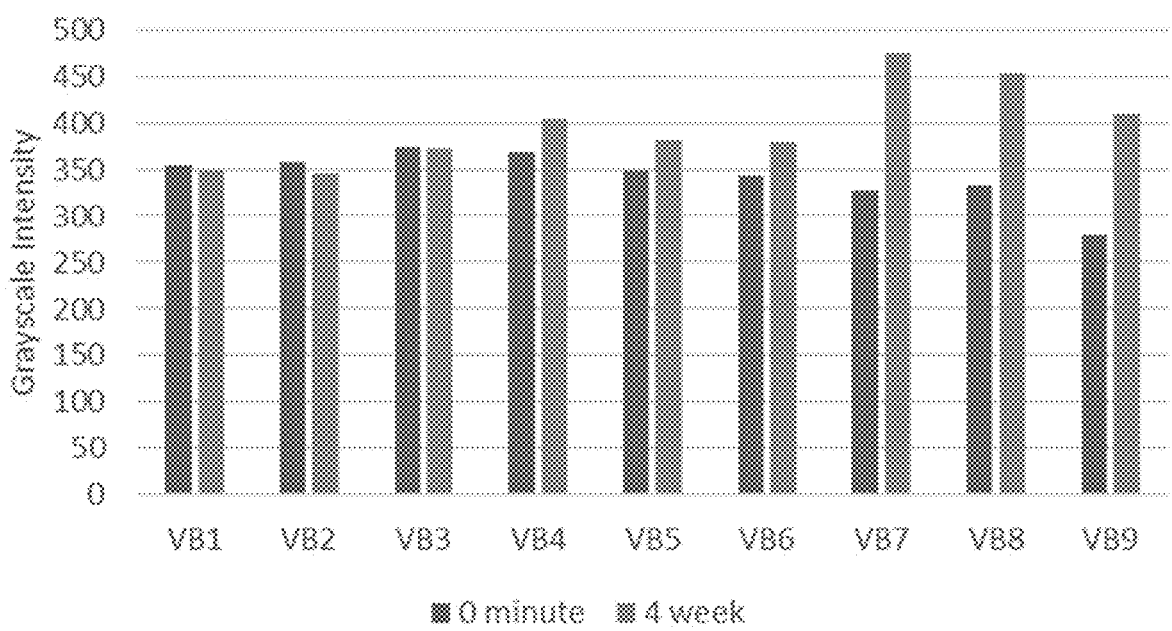
FIG. 9 is a graph showing grayscale intensity for vertebral bodies in DMSO solution initially (blue, left data in each pair) and after 4 weeks (orange, right data in each pair). Vertebral bodies 1 to 3 (VB1-3) were in 0% DMSO, VB4-6 were in 20% DMSO, and VB7-9 were in 60% DMSO.
Figure 10:
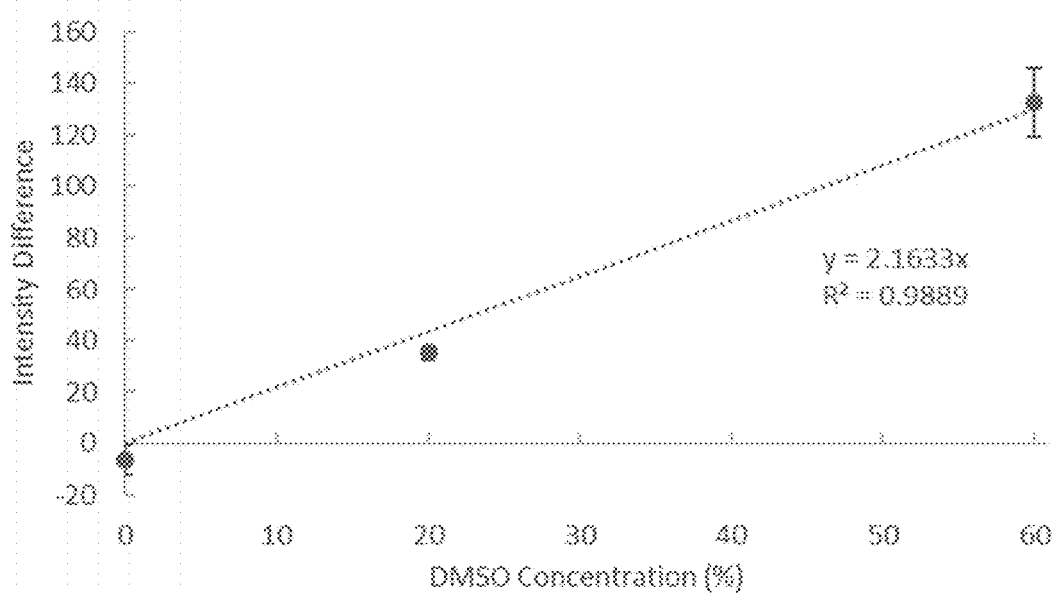
FIG. 10 is a graph showing changes in grayscale intensity for vertebral bodies in different DMSO solutions after 4 weeks. Error bars represent SD (n=3).
Figure 11:
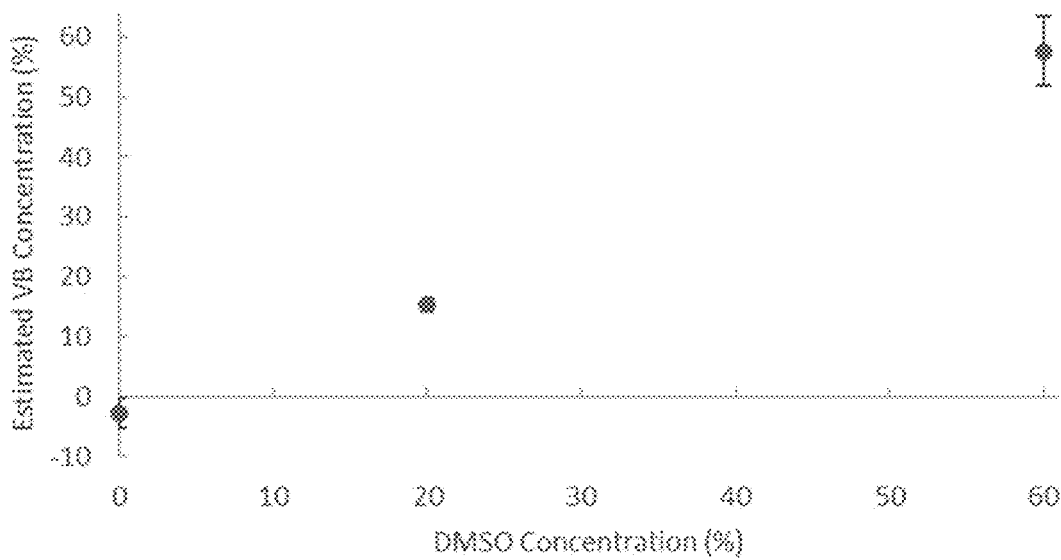
FIG. 11 is a graph showing estimated DMSO concentration within vertebral bodies (VBs) after 4 weeks in solution. Error bars represent SD (n=3).

A vertebral standard curve was then created by equilibrating vertebral bodies in either 0%, 20%, or 60% DMSO, in triplicate, for 4 weeks. For each vertebral bodies, a single, volume-averaged grayscale intensity was measured initially (t=0 minutes) and at 4 weeks (FIG. 9). The difference between the final and initial intensities were determined (FIG. 10). The data shows a linear increase in the change in intensity as DMSO concentration increases. And, these data can be used to estimate the concentration within each vertebral body using the DMSO solution standard curve model and assuming a porosity of 0.4 (FIG. 11). The mean±SD concentration in the vertebral bodies (VBs; n=3) were −2.7±2.4%, 15.3±1.1%, and 57.6±5.8% for 0%, 20%, and 60% DMSO solutions, respectively. This data show that it is possible to estimate the DMSO concentration in vertebral bodies using changes in grayscale intensity.

In the above imaging experiments, for each vertebral body, the following method was used. A region of interest (ROI) was defined around a vertebral body using masks made in Mimics medical imaging software. Air bubbles present in the vertebral bodies were isolated and removed from the ROI. Images were batch processed in ImageJ to measure area and intensity of each slice for the entire vertebral volume. The volume-averaged intensity for each time point was determined. And, the change in greyscale intensity was converted to DMSO concentration using the standard curve.

In some cases, the above-described method comprises a step of increasing the pressure in the closed container comprising a cryoprotectant to above 760 mmHg by introducing a compressed gas (e.g., nitrogen, xenon, $CO_2$, argon, $H_2S$, or helium), a gas released by sublimation (e.g., $CO_2$ via dry ice), or a gas provided by evaporation (e.g., nitrogen via liquid nitrogen), thereby permeating gas into the cadaver bone. Alternately, rather than placing a cadaver bone in closed container comprising a cryoprotectant solution, the cadaver bone in placed is a closed container that lacks a cryoprotectant solution. In this alternative, the method comprises a step of increasing the pressure in the closed container (which lacks a cryoprotectant solution) to above 760 mmHg by introducing a compressed gas (e.g., nitrogen, xenon, $CO_2$, argon, $H_2S$, or helium), a gas released by sublimation (e.g., $CO_2$ via dry ice), or a gas provided by evaporation (e.g., nitrogen via liquid nitrogen), thereby permeating gas into the cadaver bone. In a later step, a cryoprotectant solution is added to the closed container. Without wishing to be bound by theory, increasing the pressure in the closed container by introducing a compressed gas (e.g., nitrogen, xenon, $CO_2$, argon, $H_2S$, or helium), a gas released by sublimation (e.g., $CO_2$ via dry ice), or a gas provided by evaporation (e.g., nitrogen via liquid nitrogen) promotes infiltration of the cryoprotectant solution into the cadaver bone. In embodiments, the gas is $CO_2$, e.g., compressed $CO_2$. In some embodiments, the gas is nitrogen, e.g., compressed nitrogen.

Figure 12:
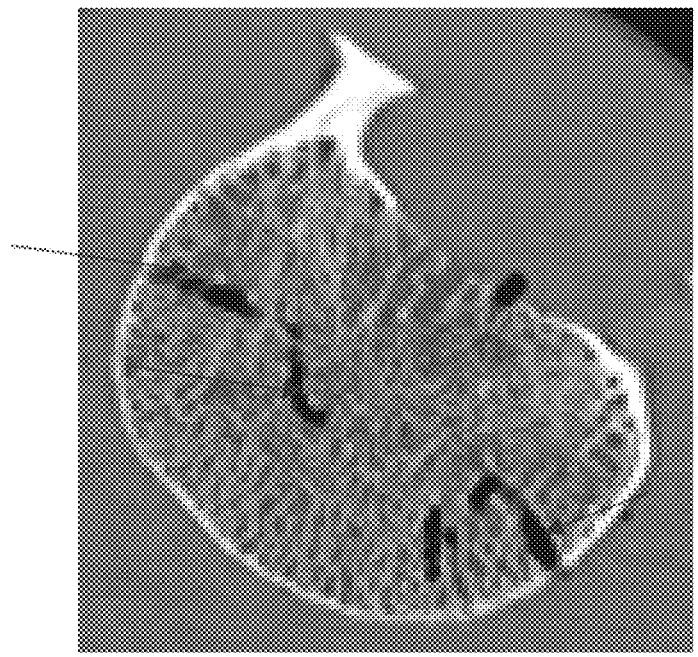
FIG. 12 is a computed tomography (CT) image showing air bubbles (black spots, some indicated by arrows) within a vertebral body.

Without wishing to be bound by theory, it is expected that the vacuum cycling process of the present disclosure removes air bubbles within a vertebral body (see FIG. 12). Further, while under vacuum, the volume of air bubbles should increase due to the much lower pressure within the vacuum chamber.

To test whether bubble volume increases under vacuum and whether bubble volume decreases after vacuum cycling, the total bubble volume within a vertebral body was measured at 0 minutes (at atmospheric pressure and before vacuum cycling), at 5 minutes (while under vacuum pressure but not long after beginning), and at the end of vacuum cycling (once again at atmospheric pressure). Comparing the bubble volumes at 0 minutes and 5 minutes can be used to test changes in bubble volume can be detected under vacuum and comparing 0 minutes and after vacuum cycling can be used to detect whether air bubbles are removed during vacuum cycling.

Figure 13A:
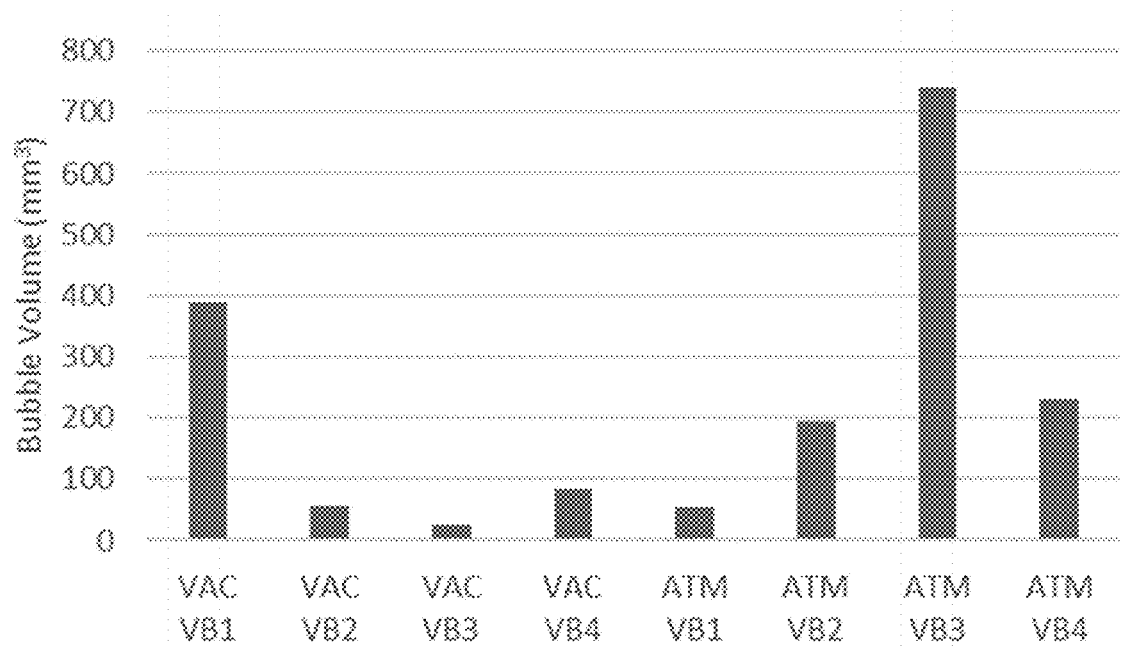
FIG. 13A is a graph showing initial bubble volumes within eight vertebral bodies (VBs).
Figure 13B:
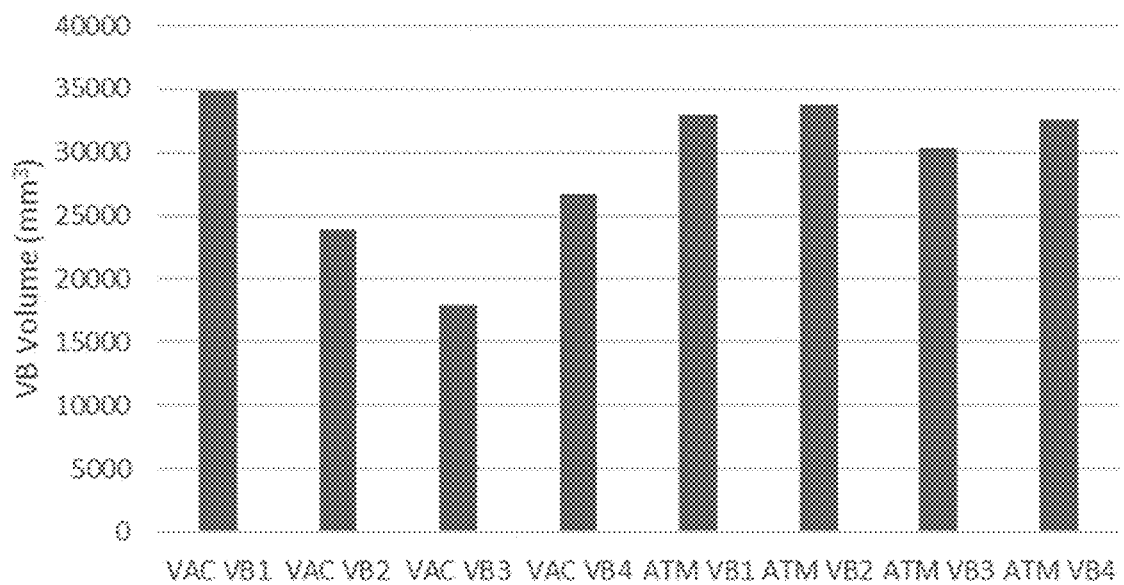
FIG. 13B is a graph showing volumes of the eight vertebral bodies (VBs).
Figure 13C:
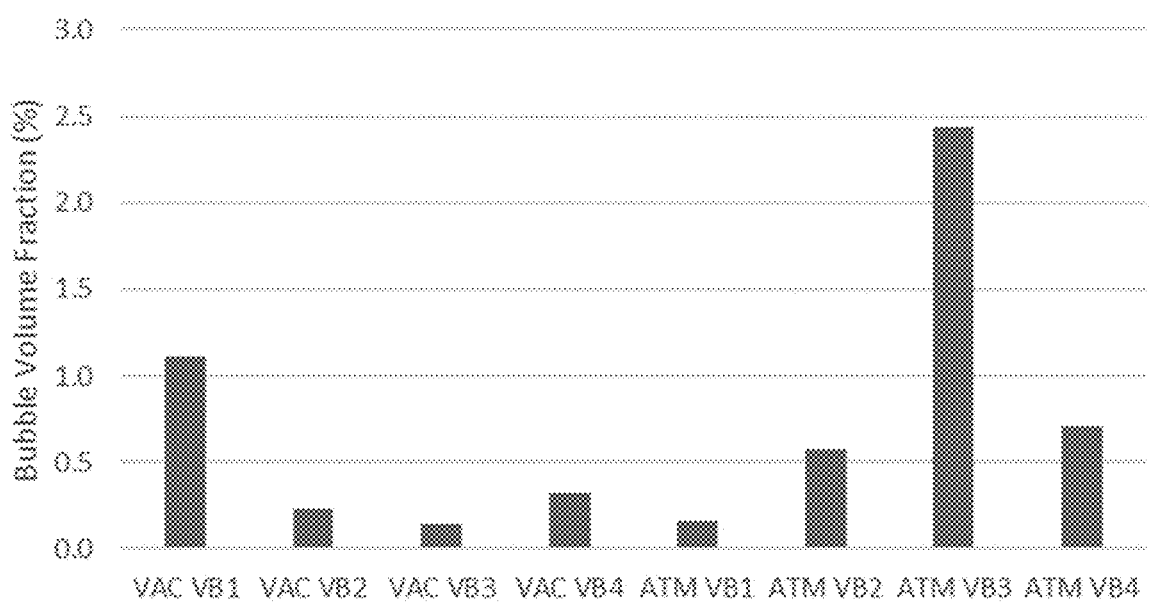
FIG. 13C is a graph showing initial bubble volume fraction within the eight vertebral bodies.
Figure 14A:
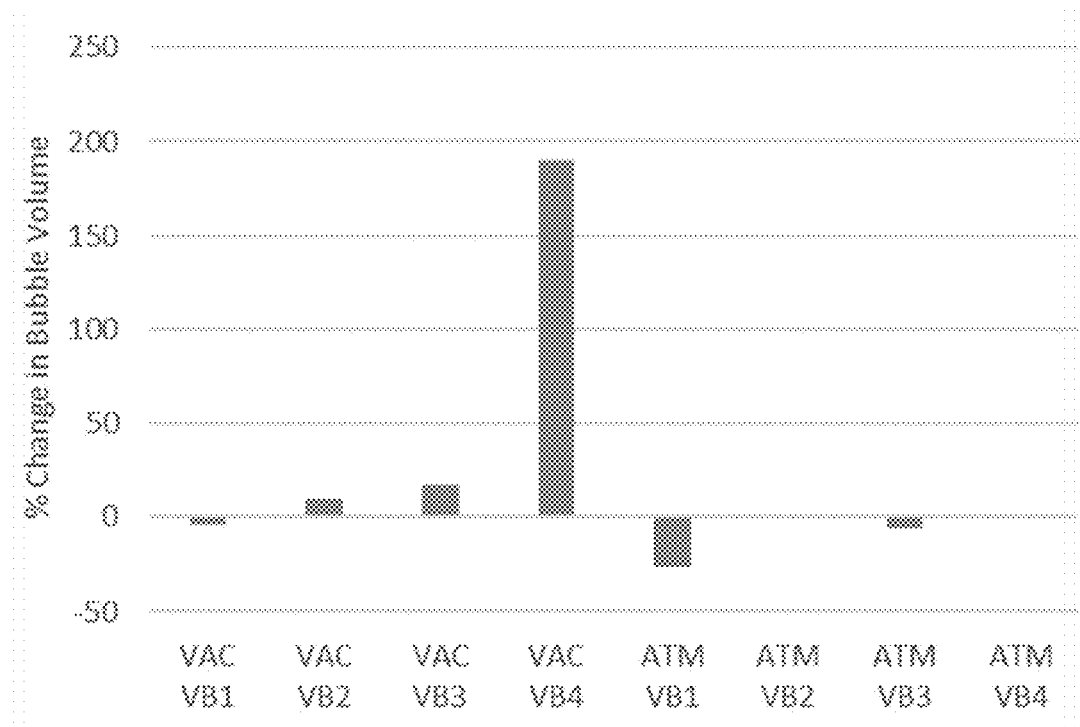
FIG. 14A is a graph showing % change in the bubble volume after 5 minutes when vertebral bodies are under vacuum.
Figure 14B:
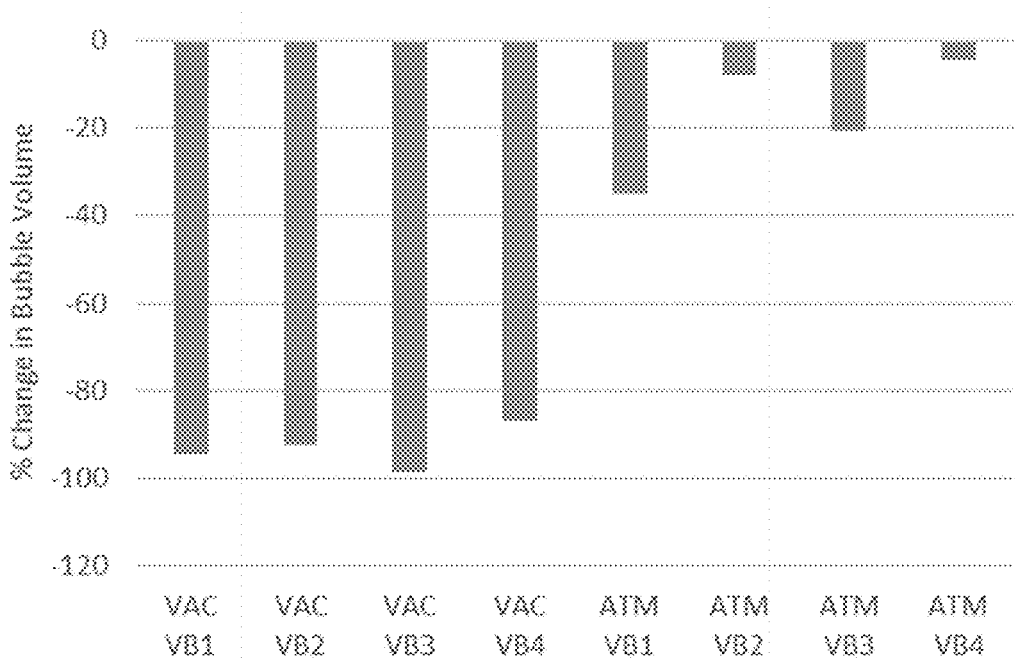
FIG. 14B is a graph showing % change in the vertebral bodies after 30 minutes of vacuum cycling.

In these experiments, dry ice carbonated vertebral bodies exposed to 40% DMSO for 30 minutes was chosen for bubble volume comparisons. The time points used were 0 minutes, 5 minutes, and 30 minutes. The initial bubble volume within the eight vertebral bodies varied from 25.4 $mm^3$ to 740.4 $mm^3$ (FIG. 13). The volume of the eight vertebral bodies varied from 18.0 mL to 34.9 mL (FIG. 14). The volume fraction that the air bubbles occupied within the vertebral bodies was less than 2.5% with most bubble volume fractions being less than 1% (FIG. 15). Four vertebral bodies were exposed to vacuum (VAC VB1 to VAC VB4) and four remained at atmospheric pressure (ATM VB1 to ATM VB4)

The % change in bubble volume after 5 minutes varied from −26.6% to 190.1% for the individual vertebral bodies (FIG. 16). The average±SD % change for the vertebral bodies under vacuum (VAC) was 53.1±91.8% while for the atmospheric vertebral bodies (ATM) it was −8.1±12.6%. The % change in bubble volume after 30 minutes of vacuum cycling varied from −4.6% to −98.7% (FIG. 17). The average±SD % change for the vertebral bodies that experienced the vacuum cycling was −93.2±4.9% while those vertebral bodies that only experienced atmospheric pressures had a % change of −17.0±13.9%. These data indicate that vacuum cycling of the present disclosure remove air bubbles from the vertebral bodies.

The methods of this example provide about 1% more viable extracted bone marrow cells to about 100% more viable extracted bone marrow cells, about 101% more viable extracted bone marrow cells to about 200% more viable extracted bone marrow cells, about 2-fold more viable extracted bone marrow cells to about 10-fold more viable extracted bone marrow cells, about 10-fold more viable extracted bone marrow cells to about 100-fold more viable extracted bone marrow cells, about 100-fold more viable extracted bone marrow cells to about 1000-fold more viable extracted bone marrow cells, or about 1000-fold more viable extracted bone marrow cells to about 10000-fold more viable extracted bone marrow cells relative to a method lacking a combination of features as disclosed in this example. In some embodiments, the extracted bone marrow cells are hematopoietic stem cells (HSCs; CD34+ cells) and/or mesenchymal stromal/stem cells (MSCs).

Example 2: An Illustrative Method for Rapidly Warming Cryopreserved Cadaver Bone In this example, a cryopreserved cadaver bone was rapidly warmed and using conditions that promote later extraction of bone marrow from the cadaver bone.

A cryopreserved cadaver bone for extraction of bone marrow was obtained. In one instance, a cryopreserved cadaver bone, which was processed by the illustrative method of Example 1, was obtained from the chamber containing liquid nitrogen and/or liquid nitrogen vapor.

The cryopreserved cadaver bone was then divided into generally sector-shaped pieces using a manual bone-cutting device that was capable of generating up to 1000 lbf when less than 50 lbf is applied. Such a manual bone-cutting device is described in US 2019/0343112, the contents of which is hereby incorporated by reference in its entirety.

The sector-shaped fragments of the cryopreserved bone were then transferred into a vessel containing warmed grinding medium. The warmed grinding medium had a temperature of from about 35° C. to about 45° C. The grinding medium was kept at the warmed temperature using a hot plate. The fragments of the cryopreserved bone remained in the warmed grinding media for a time sufficient to warm the cadaver bone fragments to a surface temperature of about 20° C. In some instances, it took about one minute to about five minutes to warm the cadaver bone fragments to a surface temperature of about 20° C. Sometimes, it took less than a minute.

The grinding medium comprised a nuclease, human serum albumin (HSA), heparin, and an electrolyte medium, e.g., Benzonase®, HSA, heparin, and PLASMA-LYTE A. In one instance, the grinding medium comprised PLASMA-LYTE as a base with 10 U/mL heparin, 2.5% human serum albumin (HSA), and 3 U/mL Benzonase® reagent.

The change in temperature of cadaver bone during fast warming is shown in FIG. 15.

The methods of this example provide about 1% more viable extracted bone marrow cells to about 100% more viable extracted bone marrow cells, about 101% more viable extracted bone marrow cells to about 200% more viable extracted bone marrow cells, about 2-fold more viable extracted bone marrow cells to about 10-fold more viable extracted bone marrow cells, about 10-fold more viable extracted bone marrow cells to about 100-fold more viable extracted bone marrow cells, about 100-fold more viable extracted bone marrow cells to about 1000-fold more viable extracted bone marrow cells, or about 1000-fold more viable extracted bone marrow cells to about 10000-fold more viable extracted bone marrow cells relative to a method lacking a combination of features as disclosed in this example. In some embodiments, the extracted bone marrow cells are hematopoietic stem cells (HSCs; CD34+ cells) and/or mesenchymal stromal/stem cells (MSCs).

Example 3: An Illustrative Method for Extracting Bone Marrow Cells from Cryopreserved Cadaver Bone In this example, fast warmed, previously cryopreserved cadaver bone is ground to extract bone marrow cells.

The fast-warmed fragments of cadaver bone of Example 2 are ground in a bone grinder to obtain ground cadaver bone in a slurry with grinding medium. In some cases, the ground cadaver bone slurry is agitated, e.g., with an orbital shaker, to promote separation of the bone marrow cells from ground cadaver bone.

The ground cadaver bone is filtered, e.g., through a No. 40 (425 μm) sieve that is stacked on top of a No. 80 (177 μm) sieve. The filtrate is diluted with additional grinding media and the, thus produced, diluted bone marrow cell product is further filtered.

The ground bone trapped by the filters is retained as captured ground bone for additional processing.

In some instances, fat is removed from the diluted bone marrow cell product. For this, the diluted bone marrow cell product is centrifuged such that a fat layer is formed. The fat layer is collected an discarded.

The bone marrow cells extracted from the warmed cadaver bone fragments comprise hematopoietic stem cells (HSCs; CD34+ cells) and mesenchymal stromal/stem cells (MSCs). In some embodiments, at least about 50% of the extracted bone marrow cells or a derivative thereof are viable, e.g., at least about at least about 70% of the extracted bone marrow cells or a derivative thereof are viable. The number of the extracted bone marrow cells or a derivative thereof extracted from the warmed cadaver bone fragments is at least about 50% of the number extracted from a fresh cadaver bone. Notably, the number of cells with proliferative potential obtained from the warmed cadaver bone fragments is at least about 50% of the number obtained from a fresh cadaver bone.

Additional steps, devices, and systems for grinding cadaver bone fragments to yield bone marrow cell products is described in US20200325451, the entire contents of which is incorporated by reference in its entirety.

The methods of this example provide about 1% more viable extracted bone marrow cells to about 100% more viable extracted bone marrow cells, about 101% more viable extracted bone marrow cells to about 200% more viable extracted bone marrow cells, about 2-fold more viable extracted bone marrow cells to about 10-fold more viable extracted bone marrow cells, about 10-fold more viable extracted bone marrow cells to about 100-fold more viable extracted bone marrow cells, about 100-fold more viable extracted bone marrow cells to about 1000-fold more viable extracted bone marrow cells, or about 1000-fold more viable extracted bone marrow cells to about 10000-fold more viable extracted bone marrow cells relative to a method lacking a combination of features as disclosed in this example. In some embodiments, the extracted bone marrow cells are hematopoietic stem cells (HSCs; CD34+ cells) and/or mesenchymal stromal/stem cells (MSCs).

Example 4: An Illustrative Method for Extracting Vertebral Bone Adherent Mesenchymal Stromal/Stem Cells (vBA-MSCs) from Captured Ground Bone In this example, captured ground bone (e.g., after bone marrow cells have been extracted from ground cadaver bone and the ground cadaver bone has been filtered) is treated to enzymatically extract vertebral bone adherent mesenchymal stromal/stem cells (vBA-MSCs).

For this, the captured ground bone (of Example 3) is treated with a digestion solution, which comprises one or more distinct enzymes. The one or more distinct enzymes may comprise at least one collagenase and/or at least one neutral protease. The digestion solution may comprise the neutral protease at an activity of about 19.6 U/ml. The captured ground bone is treated with the digestion solution at a temperature and duration sufficient to liberate the bone adherent MSCs from the captured ground bone. The digestion solution is contacted with the captured ground bone for 2.5 hours up to about 4 hours. From this method, at least about 10 million, at least about 100 million, at least about 1 billion, or at least about 10 billion nucleated cells are extracted from the captured ground bone.

Further details of the MSC recovery process of the present disclosure are found in the technical article in Johnstone et al., "Identification and characterization of a large source of primary mesenchymal stem cells tightly adhered to bone surfaces of human vertebral body marrow cavities." *bioRxiv* 2020.05.04.076950, the entire contents of which is incorporated herein by reference.

The methods of this example provide about 1% more viable extracted bone marrow cells to about 100% more viable extracted bone marrow cells, about 101% more viable extracted bone marrow cells to about 200% more viable extracted bone marrow cells, about 2-fold more viable extracted bone marrow cells to about 10-fold more viable extracted bone marrow cells, about 10-fold more viable extracted bone marrow cells to about 100-fold more viable extracted bone marrow cells, about 100-fold more viable extracted bone marrow cells to about 1000-fold more viable extracted bone marrow cells, or about 1000-fold more viable extracted bone marrow cells to about 10000-fold more viable extracted bone marrow cells relative to a method lacking a combination of features as disclosed in this example. In some embodiments, the extracted bone marrow cells are hematopoietic stem cells (HSCs; CD34+ cells) and/or mesenchymal stromal/stem cells (MSCs).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for warming cadaver bone for providing bone marrow or a derivative thereof, the method comprising:
    obtaining a cryopreserved cadaver bone;
    dividing the cryopreserved cadaver bone to obtain fragments of the cryopreserved bone; and
    transferring the fragments of the cryopreserved bone into a grinding medium having a temperature of from about 35° C. to 45° C. for a time sufficient to warm the cadaver bone fragments to a surface temperature of about 20° C.

2. The method of claim 1, wherein the cryopreserved cadaver bone has a temperature of at least below 0° C. when dividing into fragments.

3. The method of claim 1, wherein the cadaver bone fragments are warmed to a surface temperature of about 20° C. at a rate of from about 100° C./min to about 500° C./min.

4. The method of claim 3, wherein the warming rate is greater than about 300° C./min.

5. The method of claim 3, wherein the warming rate is from about 400° C./min to about 500° C./min.

6. The method of claim 3, wherein the warming rate prevents ice recrystallization during thawing of the bone fragments.

7. The method of claim 1, wherein the grinding medium has a temperature of about 37° C. to about 40° C. when the fragments of the cryopreserved bone are transferred to the grinding medium.

8. The method of claim 1, wherein the grinding medium comprises two or more of a nuclease, human serum albumin (HSA), heparin, an electrolyte medium, and a growth media.

9. The method of claim 1, further comprising a step of grinding warmed cadaver bone fragments to obtain ground cadaver bone.

10. The method of claim 9, further comprising a step of filtering the ground cadaver bone, thereby producing a filtered product comprising bone marrow cells and a captured ground bone.

11. The method of claim 10, further comprising a step of extracting vertebral bone adherent mesenchymal stromal/stem cells (vBA-MSCs) from the captured ground bone.

12. The method of claim 11, wherein extracting the vBA-MSCs comprises a step of contacting the captured ground bone with a digestion solution.

13. The method of claim 12, wherein the digestion solution is contacted with the captured ground bone after the step of collecting bone marrow cells.

14. The method of claim 9, further comprising a step of removing fat from an intermediate product.

15. The method of claim 9, further comprising a step of collecting bone marrow cells, thereby obtaining extracted bone marrow cells, wherein the extracted bone marrow cells comprise hematopoietic stem cells (HSCs) and mesenchymal stromal/stem cells (MSCs).

16. The method of claim 15, wherein at least about 50% of the extracted bone marrow cells or a derivative thereof are viable.

17. The method of claim 16, wherein at least about 70% of the extracted bone marrow cells or a derivative thereof are viable.

18. The method of claim 15, wherein the number of the extracted bone marrow cells or a derivative thereof extracted from the warmed cadaver bone fragments is at least about 50% of the number extracted from a fresh cadaver bone.

19. The method of claim 15, wherein the number of viable CD34+ cells extracted from the warmed cadaver bone fragments is at least about 70% of the number extracted from a fresh cadaver bone.

20. The method of claim 15, wherein the number of cells with proliferative potential obtained from the warmed cadaver bone fragments is at least about 50% of the number obtained from a fresh cadaver bone.

21. The method of claim 15 wherein at least about 10 million nucleated cells are extracted from the captured ground bone.

22. A method comprising:
(a) placing a cadaver bone in a closed container comprising a cryoprotectant solution;
(b) reducing the pressure in the closed container and, optionally, holding the closed container at reduced pressure, to remove at least a portion of the water present in the cadaver bone;
(c) raising the pressure in the closed container and holding the closed container at a raised pressure to allow infiltration of the cryoprotectant solution into the cadaver bone;
(d) removing the cadaver bone from the closed container;
(e) chilling the cadaver bone to a temperature of at least below 0° C., thereby cryopreserving the cadaver bone;
(f) storing the cryopreserved cadaver bone at a temperature of at least below 0° C.;
(g) dividing the cryopreserved cadaver bone to obtain fragments of the cryopreserved bone; and
(h) transferring the fragments of the cryopreserved bone into a grinding medium having a temperature of from about 35° C. to about 45° C. for a time sufficient to warm the cadaver bone fragments to a surface temperature of about 20° C.

* * * * *

UNITED STATES PATENT AND TRADEMARK OFFICE
CERTIFICATE OF CORRECTION

PATENT NO. : 11,896,005 B2
APPLICATION NO. : 18/155657
DATED : February 13, 2024
INVENTOR(S) : Erik J. Woods It is certified that error appears in the above-identified patent and that said Letters Patent is hereby corrected as shown below:

On the Title Page

Column 2 (Item (56) Other Publications), Line 9, delete "Hyopthermal" and insert -- Hypothermal --.

Page 4, Column 1 (Item (56) Other Publications), Line 39, delete "g000ds" and insert -- goods --.

Page 4, Column 2 (Item (56) Other Publications), Line 24, delete "postmordem" and insert -- postmortem --.

Page 4, Column 2 (Item (56) Other Publications), Line 25, delete "cadavric" and insert -- cadaveric --.

In the Specification

Column 9, Line 43, delete "foramamide;" and insert -- formamide; --.

Column 9, Line 45, delete "ribotol;" and insert -- ribitol; --.

Column 17, Line 25, delete "f2grinding" and insert -- grinding --.

Column 34, Line 65, delete "foramamide;" and insert -- formamide; --.

Column 34, Line 67, delete "ribotol;" and insert -- ribitol; --.

Column 35, Line 60, delete "equation" and insert -- equation. --.

Column 37, Line 19, after "VB4)" insert -- . --.

In the Claims

Column 42, Line 9 (Approx.), delete "claim 15" and insert -- claim 15, --.

Signed and Sealed this
Thirteenth Day of August, 2024

Katherine Kelly Vidal
*Director of the United States Patent and Trademark Office*